United States Patent
Mukherjee et al.

(10) Patent No.: US 12,194,444 B2
(45) Date of Patent: Jan. 14, 2025

(54) PROCESS AND CATALYST TO CONVERT METHANOL AND TOLUENE TO STYRENE

(71) Applicant: Exelus Inc., Fairfield, NJ (US)

(72) Inventors: Mitrajit Mukherjee, Fairfield, NJ (US); Vamsi Vadhri, Fairfield, NJ (US)

(73) Assignee: Exelus Inc., Fairfield, NJ (US)

( * ) Notice: Subject to any disclaimer, the term of this patent is extended or adjusted under 35 U.S.C. 154(b) by 0 days.

(21) Appl. No.: 17/542,293

(22) Filed: Dec. 3, 2021

(65) Prior Publication Data

US 2022/0193643 A1  Jun. 23, 2022

Related U.S. Application Data

(60) Provisional application No. 63/121,203, filed on Dec. 3, 2020.

(51) Int. Cl.
| | |
|---|---|
| *C07C 2/86* | (2006.01) |
| *B01J 8/02* | (2006.01) |
| *B01J 29/08* | (2006.01) |
| *B01J 37/02* | (2006.01) |
| *B01J 37/30* | (2006.01) |
| *B01J 38/12* | (2006.01) |
| *C07C 41/09* | (2006.01) |

(52) U.S. Cl.
CPC ............... *B01J 29/087* (2013.01); *B01J 8/02* (2013.01); *B01J 29/082* (2013.01); *B01J 37/0207* (2013.01); *B01J 37/30* (2013.01); *B01J 38/12* (2013.01); *C07C 2/865* (2013.01); *C07C 41/09* (2013.01); *B01J 2229/18* (2013.01); *B01J 2229/37* (2013.01); *C07C 2529/08* (2013.01)

(58) Field of Classification Search
CPC . B01J 29/082; B01J 29/087; B01J 8/02; B01J 37/0207; B01J 37/30; B01J 38/12; B01J 2229/18; B01J 2229/37; C07C 2/865; C07C 41/09; C07C 2529/08; Y02P 20/584
See application file for complete search history.

(56) References Cited

U.S. PATENT DOCUMENTS

| | | | | |
|---|---|---|---|---|
| 4,115,424 A | * | 9/1978 | Unland | B01J 29/08 502/79 |
| 4,595,785 A | * | 6/1986 | Brake | C07C 41/09 568/698 |
| 8,318,999 B2 | * | 11/2012 | Chinta | C07C 2/867 585/323 |
| 8,785,705 B2 | * | 7/2014 | Chinta | C07C 2/862 585/437 |

(Continued)

OTHER PUBLICATIONS

CPChem ("Toluene (Commercial Grade)" https://www.cpchem.com/sites/default/files/2020-05/01542633_6.pdf) (Year: 2018).*

(Continued)

*Primary Examiner* — In Suk C Bullock
*Assistant Examiner* — Jason Y Chong
(74) *Attorney, Agent, or Firm* — Frank Rosenberg

(57) ABSTRACT

The invention provides methods, catalysts and systems for producing styrene from DME and toluene. Zeolite catalysts comprising potassium, rubidium or cesium and containing at least 0.1 wt % B are described. Methods of making the catalysts are also described.

20 Claims, 3 Drawing Sheets

(56) References Cited

U.S. PATENT DOCUMENTS

2011/0270006 A1* 11/2011 Pelati ............... B01J 37/0201
502/344

OTHER PUBLICATIONS

B. K. Vasanthy, M. Palanichamy and V. Krishnasamy, Appl. Catal., A, 1996, 148, 51-61.
D. Barthomeuf, J. Phys. Chem., 1984, 88, 42-45.
W. J. Mortier, J. Catal., 1978, 55, 138-145.
S. Hocevar and B. Drzaj, J. Catal., 1982, 73, 205-215.
A. K. Ghosh and G. Curthoys, J. Catal., 1984, 86, 454-456.
L. L. Song, Z. R. Li, R. Z. Zhang, L. F. Zhao and W. Li, Catal. Commun., 2012, 19, 90-95.
A. Borgna, S. Magni, J. Sepulveda, C. L. Padro and C. R. Apesteguia, Catal. Lett., 2005, 102, 15-21.
H. Han, M. Liu, F. S. Ding, Y. R. Wang, X. W. Guo and C. S. Song, Ind. Eng. Chem. Res., 2016, 55, 1849-1858.
W. O. Alabi, B. B. Tope, R. B. Jermy, A. M. Aitani, H. Hattori and S. S. Al-Khattaf, Catal. Today, 2014, 226, 117-123.
C. Lacroix, A. Deluzarche, A. Kiennemann and A. Boyer, Zeolites, 1984, 4, 109-111.
P. Kovacheva, A. Predoeva, K. Arishtirova and S. Vassilev, Appl. Catal., A, 2002, 223, 121-128.
T. Zhang, J. Hu and S. W. Tang, Chin. J. Chem. Eng., 2018, 26, 1513-1521.
W. S. Wieland, R. J. Davis and J. M. Garces, Catal. Today, 1996, 28, 443-450.
L. L. Song, Y. Yu, Z. R. Li, S. Q. Guo, L. F. Zhao and W. Li, J. Braz. Chem. Soc., 2014, 25, 1346-1354.
Zhang, Min & Qingyun, Yuan & Miao, & Li, Yin-Sheng & Shan, & Jia, Heming. Catalysts, 2019, 9. 829-842.
Z. H. Zhang, W. L. Shan, H. Li, W. C. Zhu, N. Zhang, Y. Tang, J. H. Yu, M. J. Jia, W. X. Zhang and C. L. Zhang, J. Porous Mater., 2015, 22, 1179-1186.
H. H. Wang, B. Wang, Y. L. Wen and W. Huang, Catal. Lett., 2017, 147, 161-166.
Q. Han, P. D. Li, Y. F. Zhang, P. Lu, L. Xu, H. C. Guo and L. Xu, ChemCatChem, 2019, 11, 1610-1614.
N. Yamaguchi, A. Kobayashi, T. Sodesawa and F. Nozaki, React. Kinet. Catal. Lett., 1984, 25, 11-15.
N. Jiang, H. Jin, E. Y. Jeong and S. E. Park, J. Nanosci. Nanotechnol., 2010, 10, 227-232.
H. L. Chen, J. Ding and Y. M. Wang, Acta Phys.—Chim. Sin., 2013, 29, 1035-1040.
R. Manivannan and A. Panduranggan, Catal. Lett., 2002, 81, 119-124.
V. R. Vijayaraghavan and K. J. A. Raj, J. Mol. Catal. A: Chem., 2004, 207, 41-50.
B. Wang, W. Huang, Y. L. Wen, Z. J. Zuo, Z. H. Gao and L. H. Yin, Catal. Today, 2011, 173, 38-43.
B. Wang, W. Huang and Y. Wen, Energy Sources, Part A, 2011, 33, 1933-1939.
H. Hattori, A. A. Amusa, R. B. Jermy, A. M. Aitani and S. S.Al-Khattaf, J. Mol. Catal. A: Chem., 2016, 424, 98-105.
Pecharsky, V.K. et al., "Fundamentals of Powder Diffraction and Structural Characterization of Materials," Springer Science + Business Media, Inc., New York, 2005.
Perego, Carlo et al. Catalysis Today, 2002, 73, 1-2, 3-22.
CBI_Technology_Ethylbenzene-Styrene.pdf.
J.K.F. Buijink, Jean-Paul Lange, A.N.R. Bos, A.D. Horton, F.G.M. Niele, Chapter 13, Mechanisms in Homogeneous and Heterogeneous Epoxidation Catalysis, 2008, 355-371.
Domenico Sanfilippo, Guido Capone, Alberto Cipelli, Richard Pierce, Howard Clark, Matt Pretz, Stud. Surf. Sci. Cat., 2007, 167, 505-510.
https://cen.acs.org/articles/85/i12/Styrene-Breakthrough.html.
T. Yashima, K. Sato, T. Hayasaka and N. Hara, J. Catal., 1972, 26, 303-312.
Zhe Hong, Chuanfang Xiong, Guoqing Zhao, Zhirong Zhu. Catal. Sci. Technol., 2019, 9, 6828-6840.
E. Mielczarski and M. E. Davis, Ind. Eng. Chem. Res., 1990, 29, 1579-1582.
A. Philippou and M. W. Anderson, J. Am. Chem. Soc., 1994, 116, 5774-5783.
H. Hattori, Appl. Catal., A, 2015, 504, 103-109.
J. Jiang, G. Z. Lu, C. X. Miao, X. Wu, W. H. Wu and Q. Sun, Microporous Mesoporous Mater., 2013, 167, 213-220.
A. E. Palomares, G. EderMirth and J. A. Lercher, J. Catal., 1997, 168, 442-449.
H. Itoh, A. Miyamoto and Y. Murakami, J. Catal., 1980, 64, 284-294.
P. D. Li, Q. Han, X. M. Zhang, Y. Y. Yuan, Y. F. Zhang, H. C. Guo, L. Xu and L. Xu, Catal. Sci. Technol., 2018, 8, 3346-3356.
B. B.Tope, W. O. Alabi, A. M. Aitani, H. Hattori and S. S. Al-Khattaf, Appl. Catal., A, 2012, 443, 214-220.
M. Hunger, U. Schenk and J. Weitkamp, J. Mol. Catal. A: Chem., 1998, 134, 97-109.
S. T. King and J. M. Garces, J. Catal., 1987, 104, 59-70.
Tawan Sooknoi, John Dwyer, Studies in Surf. Sci. Cat., 1995, 97, 423-429.
A. E. Palomares, G. Eder-Mirth, M. Rep and J. A. Lercher, J. Catal., 1998, 180, 56-65.
A. Borgna, J. Sepulveda, S. I. Magni and C. R. Apesteguia, Appl. Catal., A, 2004, 276, 207-215.
Hattori, Hideshi & Alabi, Wahab & Jermy, Rabindran & al-khattaf, Sulaiman. Catalysis Letters, 2013, 143. 1025-1029.
H. Han, M. Liu, X. W. Nie, F. S. Ding, Y. R. Wang, J. J. Li, X. W. Guo and C. S. Song, Microporous Mesoporous Mater., 2016, 234, 61-72.
H. Itoh, T. Hattori, K. Suzuki and Y. Murakami, J. Catal., 1983, 79, 21-33.
H. H. Chen, X. C. Li, G. Q. Zhao, H. B. Gu and Z. R. Zhu, Chin. J. Catal., 2015, 36, 1726-1732.
R. Manivannan and A. Pandurangan, Appl. Clay Sci., 2009, 44, 137-143.
Y. Wang, M. Y. Zhu, L. H. Kang and B. Dai, Microporous Mesoporous Mater., 2014, 196, 129-135.
M. L. Unland, J. Phys. Chem., 1978, 82, 580-583.
J. Garcés, G. E. Vrieland, S. Bates, F. Scheidt—1985, Studies Surf. Sci. Cat., 20, 67.
H. Vinek, M. Derewinski, G. Mirth, J.A. Lercher, Applied Catalysis, 1991, 68, 1, 277-284.
N. Giordano, L. Pino, S. Cavallaro, P. Vitarelli and B. S. Rao, Zeolites, 1987, 7, 131-134.
W. S. Wieland, R. J. Davis and J. M. Garces, J. Catal., 1998, 173, 490-500.
H. Lee, S. Lee, R. Ryoo and M. Choi, J. Catal., 2019, 373, 25-36.
X. S. Wang, G. Wang, D. M. Shen, C. B. Fu and M. Wei, Zeolites, 1991, 11, 254-257.
M. D. Sefcik, J. Am. Chem. Soc., 1979, 101, 2164-2170.
G. Madhavi, S. J. Kulkarni and K. V. Raghavan, J.Porous Mater., 2007, 14, 379-385.
T. Yashima, Y. Ushida, M. Ebisawa and N. Hara, J. Catal., 1975, 36, 320-326.
X. S. Liu, K. K. Iu and J. K. Thomas, J. Phys. Chem., 1994, 98, 7877-7884.
J. Engelhardt, J. Szanyi and J. Valyon, J. Catal., 1987, 107, 296-306.

* cited by examiner

PROCESS AND CATALYST TO CONVERT METHANOL AND TOLUENE TO STYRENE

RELATED APPLICATION

This application claims the priority benefit of U.S. Provisional Patent Application No. 63/121,203 filed Dec. 3, 2020.

BACKGROUND

Styrene is an important monomer used in a variety of plastic products. In terms of monomer production rate, styrene ranks fourth in the US behind ethylene, vinyl chloride and propylene. Global styrene demand was estimated at $47 billion in 2019 and growing 3-5% annually.

Styrene is made conventionally by alkylation of benzene with ethylene. The resulting ethylbenzene (EB) is then catalytically dehydrogenated to styrene monomer (SM) in the presence of steam in a fixed bed, radial flow reactor system over an iron-oxide catalyst at 625° C. The reaction is favored by low pressures and is generally conducted under vacuum. The overall reaction is endothermic with heat supplied by steam, injected at 900° C. into the adiabatic reactors. Because the reaction is endothermic and requires such a high operating temperature, styrene plants use vast amounts of energy leading to high levels of GHG emissions.

An alternate synthetic route to styrene has been researched for over 35 years: the alkylation of the side chain of toluene with methanol. This route has two practical benefits—a steep reduction in feedstock costs (economic) and avoiding the energy intensive dehydrogenation reaction (environmental). The overall reaction is shown below.

$$CH_3OH \rightarrow HCHO + H_2$$

$$Toluene + HCHO \rightarrow Styrene + H_2O$$

2.1 Scheme of Reactions:

The toluene side chain reaction with methanol involves a number of reactions (see Scheme 1). As shown below, styrene forms via a reaction between toluene and formaldehyde which forms from the decomposition of methanol. Ethylbenzene can form from styrene either via hydrogenation[8] or hydrogen transfer from methanol[25], directly via a dehydro-condensation reaction between toluene and methanol[9] resulting in loss of raw material. Additionally, formaldehyde can further decompose into CO and H2. Xylenes can form either via a disproportion reaction of toluene or a ring-alkylation of toluene by methanol on acid sites. Other reactions like the water-gas shift reaction and the Boudouard reaction can also occur (not shown). Finally, subsequent alkylation of the products (ethylbenzene and styrene) can also occur yielding products like n-propyl benzene, cumene and α-methylstyrene (not shown).

Desired Reactions:

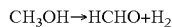

Methanol to Formaldehyde

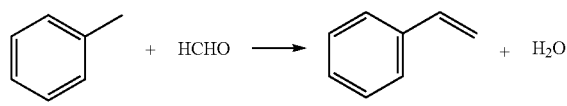

Styrene Formation

Undesired/Side Reactions:

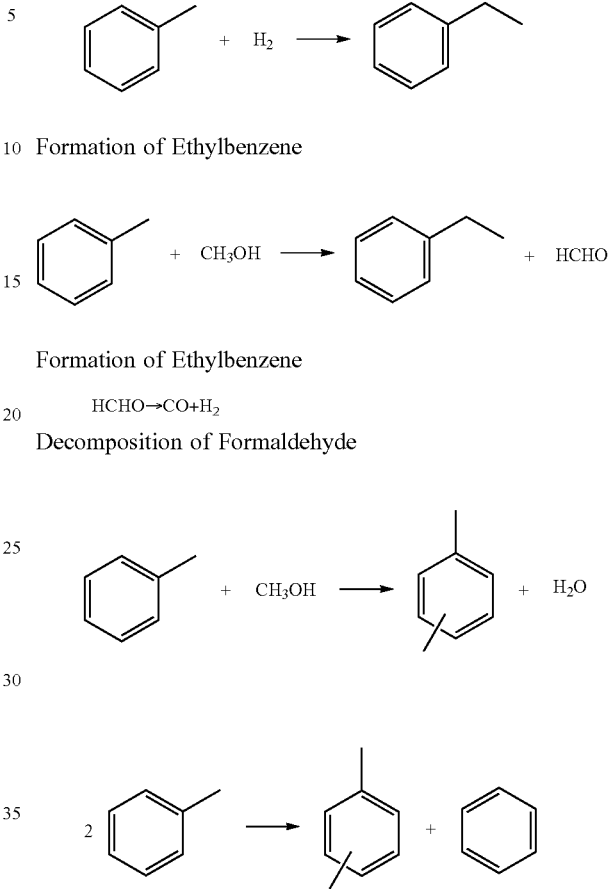

Formation of Ethylbenzene

Formation of Ethylbenzene $$HCHO \rightarrow CO + H_2$$

Decomposition of Formaldehyde

Formation of Xylenes 2.2 Reaction Mechanism:

The alkylation of the side chain of toluene with methanol involves a complicated mechanism that requires multiple types of active sites in close proximity[24]. Many catalysts have been shown to be active for the reaction though the most commonly researched ones are alkali metal-modified zeolites X and Y[2]. A number of toluene side-chain alkylation mechanisms are proposed in literature. The most commonly accepted mechanism initially suggested by Sidorenko et al.[8] and then supported by Yashima et al.[9] is that methanol is first dehydrogenated to formaldehyde which undergoes an aldol condensation type reaction with toluene yielding styrene[12,23]. The hydrogen produced in the dehydrogenation of methanol reacts with styrene to form ethylbenzene[8]. In situ IR spectroscopy and NMR studies showed the formation of surface formate species indicating that they may act as intermediates in the reaction[32,33]. These studies also showed a strong adsorption of toluene on Cs exchanged X zeolites along with the formation of ethylbenzene. Palomares et al. suggested an ionic reaction mechanism based on in situ IR spectroscopy studies of the side-chain alkylation of toluene with methanol over various alkali metal exchanged X zeolites[22].

It is widely believed that this reaction requires both acid and base sites making for a synergistic catalysis mechanism[12,13]. Typically the alkali cations act as Lewis acids, surface hydroxyl groups act as Bronsted acid sites while the framework and lattice oxygen atoms related to the base salts act as basic sites. Basic sites on zeolites are believed to promote C—H bond activation on the side chain of toluene as well as the dehydrogenation of methanol to formaldehyde, while acidic ones activate the ring and stabilize toluene. It was further suggested that while the dehydrogenation of methanol might proceed on weaker basic sites activation of toluene by abstraction of methyl H+ needs strong basic sites. On the other hand, strong acid sites yield xylenes almost exclusively due to ring methylation of toluene. A number of studies support the theory that specific catalyst geometric configurations of acidic and basic sites typically attributed to X and Y zeolites are essential for the side-chain alkylation of toluene16,24 although some non-zeolitic supports have shown some activity for this reaction59. Using selective poisoning and IR spectroscopic studies on CsY zeolites, Borgna et al. concluded that Lewis acid/Bronsted base pairs with a specific geometric configuration between the adsorbed formaldehyde and toluene are required for the side-chain reaction to proceed24.

The different steps of the proposed mechanism are presented below in more detail.

1. Methanol dehydrogenation to formaldehyde. Formaldehyde is believed to be the actual alkylating agent. The dehydrogenation occurs on basic sites and is equilibrium limited.

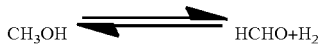

2. Activation of formaldehyde. The oxygen atom is nucleophilic and is activated with by Lewis or Bronsted acid sites forming surface formates with a positively polarized C-atom.

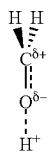

3. Activation of the toluene occurs by the interaction of π-electrons of the benzene ring with either acid sites (H+) or electropositive cation (denoted by Me+ which can be Na+, K+, Rb+, Cs+). This interaction withdraws electrons from the ring and allows for easier polarization of the methyl C—H bond. In fact, Palomares noted that this interaction increased as the cation size increased probably due to better steric match between the ring electrons and the cation. At the same time, the methyl group of toluene is activated by the strong basic sites activating the aliphatic carbon atom.

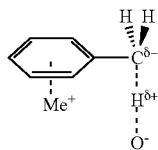

4. A base site on the catalyst removes a proton from the side chain while the side chain carbon is attacked by the electrophilic carbon from methanol (or in this case, formaldehyde) in a concerted mechanism. Aldol condensation type reaction of the activated toluene and formaldehyde forms adsorbed 2-phenylethanol.

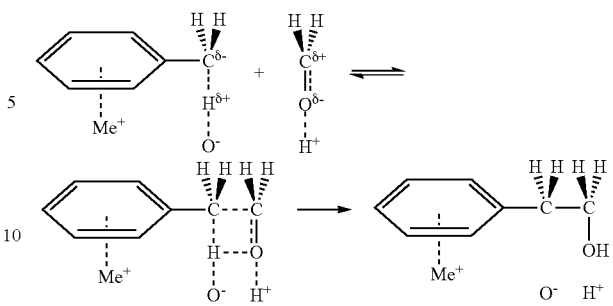

5. Dehydration of 2-phenylethanol forms styrene. This reaction typically happens on acid sites though weak basic sites have also been shown to catalyze this step. This step occurs rapidly since phenylethanol is never detected.

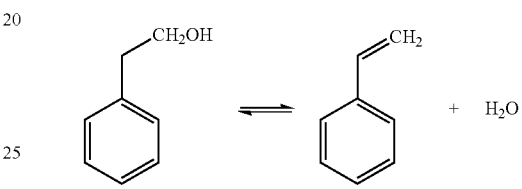

In addition to these steps a number of side reactions occur. For instance, xylenes form either via disproportionation or ring alkylation of benzene on acid sites. Formaldehyde decomposes over basic sites to CO and H2. Ethylbenzene is formed via styrene hydrogenation or through other routes. Over alkylation of styrene and ethylbenzene occurs yield heavier aromatic compounds. Boudouard reaction and water gas shift reaction can occur leading to formation of CO2.

2.3 Role of Acid-base sites: This above described mechanism needs acid sites to adsorb and stabilize the aromatic ring of toluene and the methanol oxygen while it uses the base sites for the C—H bond activation on the side chain of toluene as well as the dehydrogenation of methanol to formaldehyde. Acid sites were also found to be responsible for stabilizing formaldehyde11,16,32.

Strong basic sites are required for the methyl group activation of toluene. Usually, the basicity of zeolites could be increased by the increase in atomic number of the alkali cation and the Al/Si ratio of zeolite framework. The basicity of the NaX and NaY increases when these zeolites are modified by ion-exchange or impregnation of more electropositive cations like K, Rb or Cs or their mixture. Additionally, studies showed that as the exchange-degree of Cs, Rb or K increased over X and Y zeolites, the basicity of the zeolite increased. Xylenes are a product of benzene ring alkylation of toluene with methanol and occur over Bronsted acid sites. As the degree of exchange increased, the Bronsted acidity and number of acid sites reduced and the products of the reaction between toluene and methanol shifted from predominantly xylenes to side-chain alkylation products. However, very strong basic sites promote the undesired methanol decomposition reaction as well as the transfer hydrogenation between methanol and styrene yielding ethylbenzene. Weak basic sites were found to be unable to activate the toluene methyl group.

Many studies claim that the overall acid-base strength as defined by intermediate Sanderson electronegativity (Sint) governs the catalyst performance for side-chain alkylation of toluene36,37,47. For instance, the selectivity to ethylbenzene and methanol decomposition to CO were found to increase monotonously while xylene formation and DME production were found to decrease monotonously with reduction in Sint. The maximum selectivity to styrene however was obtained at intermediate Sint values suggesting that neither strong acidity nor strong basicity was beneficial for the reaction. However, Sint as a sole reaction parameter has been found to be limiting since studies showed that many other factors such as distance between the AlO4-tetrahedra, charge balancing cation, proximity of acid-base pairs, and presence of ion clusters and modifiers play a crucial role.

Introduction of oxides, carbonates and hydroxides of electropositive metals like Cs, Rb and K into zeolites have shown a considerable increase in the yield of side-chain alkylation products. These added clusters are believed to be stronger base sites than the same ions in the framework and contribute to increased side chain alkylation activity though the selectivity of styrene reduced in their presence18,54. However, both Cs framework ions and Cs2O cluster species are believed to act synergestically for the side-chain akylation of toluene and the two species had different roles in the reaction pathway17,26. According to the authors, Cs ions were responsible for activation of toluene and increased basicity of the oxygen atoms while Cs2O clusters were instrumental in methanol dehydrogenation and CO formation. Conversely, when the zeolites were washed after ion-exchange or impregnation, the side-chain alkylation activity was reduced suggesting the importance of excess alkali hydroxides for this reaction76.

On the other hand, Bronsted acid sites in NaY (weak basic zeolites) were found to be catalyze the formation of xylenes and displayed almost no side-chain alkylation activity. Zeolites like ZSM-5 could catalyze only the ring alkylation of toluene even if they were impregnated with strongly basic cations like Cs35. Addition of elements like B and P and their derivative compounds have shown an increase in selectivity to desired compounds. While many theories are proposed for this observation, these elements are thought to selectively poison some of the strong basic sites which cause the undesirable reactions like formation of ethylbenzene and decomposition of formaldehyde without affecting the side-chain alkylation activity32,37. A balanced combination of strong and weak basic sites along acid sites is thus desirable for a high yield of styrene from the reaction of toluene and methanol.

2.4 Ethylbenzene formation: Ethylbenzene is simultaneously produced with styrene in all the cases reported. For commercial reasons, a high selectivity of styrene relative to ethylbenzene is desirable. Hence the exact mechanism and factors for formation of ethylbenzene are studied so that steps can be taken to minimize its formation. Sidorenko et al. suggested that styrene is formed by the reaction of toluene with formaldehyde formed from the dehydrogenation of methanol and the by-product H2 reacts with styrene to form ethylbenzene8.

Other studies suggest that the hydrogenating agent is not gaseous hydrogen is either methanol or formaldehyde25,34. Hattori et al. found that this pathway was enhanced in the presence of excess Cs2O clusters and was inhibited by the addition of zirconium borate25. The authors reported an increase in selectivity of ethylbenzene in the presence of gaseous hydrogen but they also believe that the contribution of styrene hydrogenation with gaseous hydrogen is small compared to transfer hydrogenation of styrene with methanol. Han et al. however proposed that both modes of styrene hydrogenation made significant contributions to the formation of ethylbenzene26.

Sooknoi and Dwyer21 suggested that ethylbenzene could also form from the hydrogenolysis of 2-phenylethanol which is considered to be an intermediate in styrene formation. Other studies postulate that ethylbenzene forms not through styrene as an intermediate but directly via a dehydro-condensation reaction between toluene and methanol9. Higher ethylbenzene to styrene ratios were observed when methanol was used as an alkylating agent than formaldehyde and Yashima et al. used this as evidence to support the theory of direct formation of ethylbenzene from the reaction of toluene and methanol9. However, Hattori et al. consider this unlikely and believe that the increased ethylbenzene formation in the presence of methanol is due to increased transfer hydrogenation of styrene with methanol25.

Li et al. studied the reaction mechanism over a series of catalysts based on NaX zeolites and concluded that the primary route of formation of ethylbenzene varied with the degree of exchange (ED) of the Cs ions17. They reported that at low Cs content hydride transfer between styrene and carbon deposition over Bronsted acid sites was the primary route while the transfer hydrogenation of styrene of methanol or formaldehyde was the main path for the formation of ethylbenzene in catalysts with high Cs content. Whatever the exact mechanism, strong basic sites are believed to be responsible for ethylbenzene formation.

2.5 Phenylethanol as an intermediate: It is often proposed that 2-phenylethanol is an intermediate in the side-chain alkylation of toluene to methanol reaction to form styrene under typical reaction conditions. Although it is never detected due to its rapid dehydration to form styrene but Density Functional Theory studies confirm its formation30. A number of studies in literature have studied the reaction of phenylethanol over acid and basic sites. It is generally believed that phenylethanol undergoes dehydrogenation over strong basic sites to form acetophenone while it undergoes dehydration over acid sites to form styrene. Sooknoi and Dwyer however suggested that 2-phenylethanol could also be an intermediate in the formation of ethylbenzene via hydrogenolysis21. They claimed that this reaction was enhanced over Cs2O clusters.

2.6 Free radical mechanism: While the above described mechanism is the most commonly accepted one, a free radical mechanism for the side-chain alkylation of toluene by methanol has also been proposed using isotope tracer studies28. According to this mechanism, toluene first forms C6H5CH2· on a basic site which then reacts with methanol to generate 2-phenylethanol—an intermediate to form styrene. Huang and Ko studied the alkylation of ethylbenze with methanol over modified X zeolites. They reported the formation of styrene, cumene, α-methylstyrene, toluene and benzene and also proposed that this reaction occurs via a free-radical mechanism.

2.7 Reaction Intermediates: Numerous spectroscopic and computational studies on the topic have been carried out which shed light on the mechanism as well as the intermediates formed on the catalyst surface. Methanol decomposition is said to yield many intermediates such as formaldehyde and surface formates, methoxide and carbonate species32,33. According to some researchers, the actual alkylating agent is formaldehyde16,23. While phenyl ethanol has never been observed as a product, Density Functional Theory studies confirm the formation of phenyl ethanol30. Studying the methanol decomposition on different alkali metal—exchanged zeolite X, Unland observed methoxide, carbonate and formate species on NaX but only found formate species on the more active KX, RbX and CsX catalysts32. While some authors considered surface formate species to be too stable and "dead end" products, others suggested that they are actually active reaction intermediates. King and Garces found that formate species were not detected on the surface of LiX and NaX zeolites which primarily carry out ring alkylation to form xylenes20. Studies also suggested that formate species can have a bidentate or a unidentate structure on catalyst surfaces and while bidentate formate undergoes decomposition to CO and H2, a unidentate formate could be an active intermediate for the alkylation reaction with toluene18,20. The observation of formate species suggested the formation of formaldehyde since surface formates result from the further oxidation of formaldehyde. However, other studies have proposed the formation of free radical formaldehyde too suggesting a possible free radical mechanism28.

3. Prior Art: Side-chain alkylation of toluene with either methanol or formaldehyde has been investigated for over four decades by researchers in both industry and academia. Yashima et al.9 described synthesis of styrene using X and Y-type of zeolites. More specifically, it is disclosed therein that alkylation of the methyl group of toluene to form styrene and ethylbenzene is effected by Na, K, Rb or Cs exchanged X- or Y-type zeolites, whereas Li exchanged zeolites of the same type effected predominantly alkylation of the benzene ring of toluene to form xylenes. Yashima et al. interpret their results as suggesting that xylene formation is attributable to the acidity of the catalyst, whereas styrene and ethylbenzene formation is attributable to the basicity of the catalyst.

Over time, various other modified zeolites have been employed as catalysts for the side-chain alkylation of toluene such as X, Y, ZSM-5, MOR, Beta and L. Results have shown that zeolites with Faujasite structure (X and Y) were more active than other zeolites like L and Beta for this reaction37. Zeolites using ZSM-5 as a precursor primarily catalyzed the ring alkylation of toluene yielding xylenes35, 39.

Basicity was proven to be a crucial factor for the reaction which allows for the polarization of the methyl group of toluene. Strong basic sites are required for the polarization and activation of the methyl group of toluene. Usually, the basicity of zeolites could be increased with increasing atomic number of the modifying alkali cation and the Al/Si ratio of zeolite framework.

Other catalytic features found to be important were pore size and microporous structure11,37. A number of studies support that the side-chain alkylation of toluene with methanol has specific steric requirements of acidic and basic sites to activate the reactant species16,24. These features are typically attributed to X and Y zeolites although some non-zeolitic supports have shown some activity for this reaction37. Non-zeolitic microporous catalysts like activated carbon with adequate basicity on the catalyst surface and proximity between base-sites and Lewis acid sites were able to provide additional interactions which facilitate the activation of toluene. Non-microporous catalysts were found to be inactive for the reaction.

3.1. Modified Faujasite Catalysts: Since only Faujasite zeolites (X and Y) could offer sufficient basicity, micropore structure and tunable acid-base properties, they were found to be the most active for the side-chain alkylation of toluene using methanol and/or formaldehyde. Of these, modified X zeolites were found to be more active than modified Y zeolites for this reaction presumably due to their higher basicity28,40-42. However, significant modifications were needed to make these zeolites active for the reaction. Typically, alkali metals, alkaline earth metals, rare earth metals, transition metals and non-metal additives have been used to modify zeolites X and Y.

The highest side-chain alkylation activity is usually shown when zeolite X is modified using alkali metals. Among them, the activity order was found to be as follows: CsX>RbX>KX>NaX 40,43,44,45. This order correlates to the increasing electropositive nature and ionic radius of the cation which in turn affects the formation and adsorption of chemical species and reduces the unfavorable Bronsted acid sites26.

The basicity of the NaX and NaY increases when these zeolites are modified by ion-exchange or impregnation of more electropositive cations like K, Rb or Cs or their mixture43-46. The overall basicity of zeolites can be quantified by value of intermediate Sanderson electronegativity (Sint)47-50. Sint values follow the order NaX>KX>CsX. Studies have shown that activity of side-chain alkylation of toluene increased with decreasing Sint values. The selectivity to ethylbenzene and methanol decomposition to CO were also found to increase monotonously while xylene formation and DME production were found to decrease monotonously with reduction in Sint. The maximum selectivity to styrene however was obtained at intermediate Sint values suggesting that neither strong acidity nor strong basicity was beneficial for the reaction37. However, Sint as a sole reaction parameter has been found to be limiting since studies showed that many other factors such as distance between the AlO4-tetrahedra, charge balancing cation, proximity of acid-base pairs, and presence of ion clusters and modifiers play a crucial role.

The alkali metal ions are added to the zeolite X either by ion-exchange or impregnation. The modification procedure affected the form in which the alkali metals existed on the zeolite. The alkali metal exists as a compound when the zeolite is modified using an impregnation procedure and as ions when an ion-exchange procedure is used54. It was postulated that the synergistic effect of Cesium ions and Cesium oxides was important for maximum styrene formation54,55,53. According to the Han et al.53, Cs ions were responsible for activation of toluene and increased basicity of the oxygen atoms while Cs2O clusters were instrumental in methanol dehydrogenation and CO formation. Numerous studies have also shown that addition of oxides, hydroxides and carbonate species of alkali metals resulted in an increase of side-chain alkylation activity presumably due to increased basicity of the catalysts with the addition of these species. However, the presence of these species also accelerated the decomposition of methanol as well as ethylbenzene formation. Conversely, when zeolites were washed after ion-exchange or impregnation, side-chain alkylation activity was reduced suggesting the importance of excess alkali hydroxides for this reaction55,45. Of all the metal precursors, alkali hydroxides were shown to be more effective than alkali metal salts19,45,51.

Apart from the choice of metal cation, the degree of exchange (ED) also affected the basicity of the faujasites and whether the predominant reaction was ring-alkylation or side-chain alkylation51,52. Song et al. studied the effect of ED of K+ ions on the reaction and found that at lower KED of alkali metal ions (<40%), ring-alkylation was the primary reaction while KED (>57%) favored side-chain alkylation51. Similar observations were made by Li et al. with CsX17. The authors note that Bronsted acidity gradually weakened with increase in CsED and completely disappeared when CsED was 45.9%. They also claim that the mechanism of reaction changed as CsED increased. At low CsED (<32.3%), toluene activation was the crucial step while at higher CsED (>32.3%), methanol dehydrogenation to form formaldehyde was the crucial step. Similarly, the mechanism of formation of ethylbenzene was also dependent on CsED. Based on their understanding, the authors recommend a CsED of around 45.9% to maximize side-chain alkylation activity and minimize styrene conversion to ethylbenzene.

Catalysts obtained by modifying zeolite X with multiple alkali metal ions were reported to exhibit higher catalytic performance than the ones modified with single alkali metal ions. Itoh et al report that addition of a small amount of Li+ improves the acid-nature of the catalyst and promotes the side-chain alkylation activity27. Jiang et al. reported that KRbCsX displayed higher methanol utilization (49.5%) than on KX (10.9%) or CsX (13.2%) alone14.

Studies were also conducted which tested the efficacy of modifying zeolite X with metals other than the alkali metals for the side-chain alkylation of toluene. SrO and BaO modified zeolite X were found to be more active for this reaction than MgO and CaO modified ones56. This was expected since Sr and Ba were more basic than Mg and Ca. Zhang et al. tested KX modified with BeO, MgO, CaO and BaO for this reaction and found that MgO modified KX was the most active57. This was postulated to be due to the decrease in strong basic sites with Mg which prevents the decomposition of formaldehyde to form CO.

3.1.1 Role of modifiers and additives: Several studies have investigated the incorporation of various modifiers and additives to side-chain alkylation catalysts to change their acid-base properties in order to improve the performance for this reaction.

Unland and Barker found that addition of B and P into alkali exchanged X and Y zeolites results in increased aromatic selectivities. They speculated that these elements neutralized strong basic sites responsible for CO formation58. This hypothesis was confirmed by various studies. Tope et al.18 and Alabi et al.54 reported that B can also be added as metal borates and proposed that metal borates, specifically $ZrB_2O_5$ and $ZnBO_4$, facilitated the formation of formaldehyde from methanol as evidenced by a distinct IR band attributed to unidentate formate formation. These metal borates were also believed to suppress the formation of ethylbenzene which forms via transfer hydrogenation of styrene with methanol leading to high styrene selectivities, as high as 93.2% with the addition of 10 wt % $ZrB_2O_5$ to CsX18. Additionally, Zhang et al. reported that addition of $BPO_4$ (boron phosphate) to CsX did not reduce the basic strength of the catalyst but reduced the number and concentration of basic sites and introduced Lewis acid sites63. The authors claimed that incorporation of $BPO_4$ improved toluene conversion and styrene selectivity and attributed this to the reduced concentration of basic sites and consequently reduced formation of bidentate formate, an intermediate to CO formation. Wang et al. reported that addition of more than 5 wt % $K_3PO_4$ to CsX zeolites enhanced side-chain alkylation activity presumably due to reduction of weak acid sites and increase in the strength and amount of middle base sites64.

Transition and rare earth metals: Transition metals too have been investigated as modifiers to improve the catalyst performance for side-chain alkylation of toluene. Das and Pramanik reported that addition of Fe—Mo to CsX improved the activity of the reaction by facilitating the formation of formaldehyde61. Zhang et al. reported that introduction of $FeO_x$ species from the decomposition of nitrate salts to CsX introduces Lewis acid sites which activate methanol and stabilize unidentate formate, inhibit bidentate formate formation, and consequently increases styrene yield62. In order to promote the dehydrogenation of methanol to formaldehyde, Lacroix et al. added Cu and Ag to CsX zeolites and reported increased side-chain alkylation yields with this modification55. Hattori et al. studied the effect of adding various transitional metal oxides (ZnO, CuO, $ZrO_2$, $MoO_2$ and $V_2O_3$) to Cs-based catalysts and reported improved toluene conversion and styrene yields with the addition of ZnO78. Song et al. also reported that addition of small amounts of $ZnO_x$ (0.8 wt %) to KX increases the conversion of toluene by almost two times from around 7% to 14%60. Based on XPS and TPD studies, the authors propose that addition of Zn increases the basicity of the framework oxygen atoms and introduces weak acidity. According to the authors, these changes to the catalyst facilitates easier formation of formaldehyde from methanol, favors formation of the desirable unidentate formate and reduces adsorption strength of toluene allowing increased methanol adsorption all of which contribute to increased side-chain alkylation products. Other studies showed that introduction of rare earth elements improved the side-chain alkylation activity. For instance, addition of La (0.5 wt %) and Ce (1 wt %) to KX increased the yield of side-chain alkylation products to 26% and 23.7% respectively compared to 19.8% of the unmodified KX catalyst58. The increase in side-chain alkylation activity was thought to be due to reduced dealumination of the zeolite with the introduction of rare-earth elements leading to its increased hydrothermal stability and higher partial charge of the $AlO_4$-tetrahedra.

3.2 Composite catalysts: Since the side-chain alkylation of toluene with methanol involves multiple steps with varying catalyst requirements, studies have been conducted to mix different catalysts for the various functionalities. Itoh et al.27 reported that addition of small amounts of Li, a Lewis acid, promoted the reaction. Wang et al.39 proposed that a mixture of KX and KZSM-5 zeolites was more active than either catalyst. They suggested that KX was responsible for activation of methyl group of toluene while KZSM-5 catalyzed the methanol conversion to formaldehyde. Similarly, Hui et al.65 noticed an improvement in methanol utilization when K20-KZSM-5 was mixed with KX.

Han et al.67 reported that the addition of $Na_2B_4O_7$ or $Cu/SiO_2$ to CsX makes an effective composite side-chain alkylation catalyst. These compounds are believed to preferably catalyze the dehydrogenation of methanol to formaldehyde and their addition to CsX improves the methanol conversion as well as the yield of styrene and ethylbenzene. However, this approach was proven to be more effective when the components were mixed in close proximity rather than when separated in a dual-bed configuration in the same reactor.

3.3 Other catalysts: Apart from the modified faujasite based catalysts, other catalysts have been designed and tested with some success. Xu et al.66 synthesized and tested an Mg modified ZSM-5/AlPO4 catalyst for side-chain alkylation of toluene and reported that it showed better stability than Mg modified NaX. The authors postulated that the new catalyst had improved diffusional characteristics which reduced coking.

Garces et al.68, Wieland et al.59 and Yamaguchi et al.69 tested Cs modified carbon-based catalysts for the side-chain alkylation reaction and reported that these catalysts were active for this reaction suggesting that zeolite structure was not a necessary condition for this reaction although the aromatic compound yields were lower than those of basic X and Y zeolites. While carbon supports do not possess the zeolitic framework, they do possess microporosity and mesoporosity which provide the required steric environment essential for the reaction. Wieland et al.59 noted that the activity of the carbon-based catalysts followed this order as expected: Cs>Rb>K and that addition of 0.5 wt % Boron increased the aromatic yields and selectivities presumably due to reduced methanol decomposition to CO.

Metal oxide catalysts have been investigated for this reaction and MgO—TiO2 and CaO—TiO2 showed higher activity than bulk MgO, NaOH—SiO2 and KOH—SiO2. Additionally, mesoporous silicalite-1 supported MgO performed better than bulk MgO catalysts and the activity increased with increase in MgO content70,71.

Various layered double hydroxides (LDH) have been studied for the side-chain alkylation of toluene29,72. Of the catalysts tested, Mg/Al LDHs were found to be effective for the formation of ethylbenzene and styrene while Co/Al, Ni/Al, Zn/Al and Cu/Al LDHs preferentially catalyzed the formation of xylenes. The side-chain alkylation activity was observed to increase with increase in Mg/Al ratio and with temperature. Surface sites with different base strength i.e. low (OH-groups), medium (Mg—O pairs) and strong (O2- anions) were found to be the active sites for this reaction.

Doping materials with nitrogen has been shown to increase the surface basicity due to increased electron donating properties. This property could be used to catalyze the side-chain alkylation of toluene with methanol. Vijayaraghavan et al. prepared active side-chain alkylation catalysts by doping AlPO4-5 zeolites with nitrogen73. Wang et al. prepared acid-base catalysts with aluminum and nitrogen from aluminum and amine by using triblock copolymer Pluronic F127 as a template and resol as framework via evaporation induced organic-organic assembly method74,75. Of these, Cat-NH(C2H5)2 has been found to be active for formation of styrene with a yield of 44.9% based on methanol. According to the authors, it is because it has the optimum distance between acid and base sites for toluene polarization as well as the right amount and strength of acid-base sites.

3.4 Catalyst stability: Despite the large number of studies on this topic, only a handful have addressed the topic of catalyst stability. The catalyst supports typically employed for the side-chain alkylation of toluene are crystalline zeolites like X and Y. Many results published on this topic usually report the fresh catalyst performance and not the results over a spent catalyst which has undergone a number of reaction-regeneration cycles. The catalytic activity usually decreases with time-on-stream due to coke formation in the form of aromatic compounds causing pore blockage as evidenced by a reduction in BET surface area[14]. This form of deactivation is reversible and can be regenerated by calcination in air. However, the steam that is generated during regeneration results in dealumination of the catalyst causing structural damage, reduced crystallinity and a gradual permanent deactivation. Efforts should be made to improve the hydrothermal stability of the catalyst and mitigate coke formation.

Glossary

Activity Parameter—To compare the catalyst performance under different conditions, the activity is quantified by the activity parameter which is the reaction rate constant described above for the side-chain alkylation reaction given below:
Activity Parameter (AP) is calculated from conversion (x) and WHSV as follows $$AP(k) = WHSV * -\ln(1-x)$$

A catalyst converting toluene with a high activity will have an activity parameter>0.02.

Selectivity Parameter—Since selectivity of styrene monomer (SM) varies with toluene conversion, a method is required to compare selectivity obtained by different catalysts under various conversions. Selectivity parameter is calculated from the ratio of the first-order rate constant of the toluene conversion to SM (k1) to the first-order rate constant of the styrene conversion to ethyl benzene (EB) (k2) and remains constant irrespective of the toluene conversion for a successive reaction given below:

A catalyst producing styrene monomer with a high selectivity will have a selectivity parameter>0.1.

The selectivity parameter (SP) (=k1/k2) is calculated from toluene conversion (x) and SM yield (y) by solving the equations shown below:

$$k1 = WHSV * -\ln(1-x)$$

$$y = [k1/(k2-k1)][e^{(-k1/WHSV)} - e^{(-k2/WHSV)}]$$

Stability Parameter—The loss of catalyst activity with time is quantified by the stability parameter which measures the rate of change of Activity Parameter with time ($AP_t$). A catalyst with high stability will have a low stability parameter value <0.005.

$$\text{Stability Parameter} = (AP_0 - AP_t)/t$$

Attrition Index: The attrition resistance of catalysts used in fluidized reactor systems are characterized by the Attrition Index determined by ASTM tests such as AJI—Air Jet Index which is the percent attrition loss at 5 hours (ASTM D5757—Standard Test Method for Determination of Attrition of FCC Catalysts by Air Jets).

Calcination Temperature—The term "calcination temperature" refers to the maximum temperature utilized as an intermediate step in the catalyst synthesis procedure intended to convert the metal salts to their oxide form.

Conversion—The term "conversion of a reactant" refers to the reactant mole or mass change between a material flowing into a reactor and a material flowing out of the reactor divided by the moles or mass of reactant in the material flowing into the reactor. For propane dehydrogenation, conversion is the mass of toluene reacted divided by the mass of toluene fed.

Exchangeable Sodium is all sodium contained in the framework of a zeolite: The basic formula for all crystalline sodium zeolites may be represented as follows:

$$(Na_2O):(Al_2O_3): x(SiO_2): y(H_2O).$$

In general, a particular crystalline zeolite will have values for x and y that fall in a definite range. The value x for a particular zeolite will vary somewhat since the aluminum atoms and the silicon atoms occupy essentially equivalent positions in the lattice. For zeolite X, an average value for x is about 2.5 with the x value falling within the range 2.5±0.5. The value of y is not necessarily an invariant for all samples of zeolites. This is true because various exchangeable ions are of different size, and, since there is no major change in the crystal lattice dimensions upon ion exchange, the space available in the pores of the zeolite to accommodate water molecules varies. The average value for y determined for zeolite X is 6. The formula for zeolite X may be written as follows:

$$(Na_2O):(Al_2O_3):2.5(SiO_2): 6(H_2O).$$

The amount of exchangeable sodium for Zeolite X can then be calculated to be 11% The formula for zeolite Y may be written as follows:

$$(Na_2O):(Al_2O_3):5(SiO_2): 8.9(H_2O).$$

"Particle size" is number-average particle size, and, for non-spherical particles, is based on the largest dimension.

Pore size—Pore size relates to the size of a molecule or atom that can penetrate into the pores of a material. As used herein, the term "pore size" for zeolites and similar catalyst compositions refers to the Norman radii adjusted pore size well known to those skilled in the art. Determination of Norman radii adjusted pore size is described, for example, in Cook, M.; Conner, W. C., "How big are the pores of zeolites?" Proceedings of the International Zeolite Conference, 12th, Baltimore, Jul. 5-10, 1998; (1999), 1, pp 409-414.

One of ordinary skill in the art will understand how to determine the pore size (e.g., minimum pore size, average of minimum pore sizes) in a catalyst. For example, x-ray diffraction (XRD) can be used to determine atomic coordinates. XRD techniques for the determination of pore size are described, for example, in Pecharsky, V. K. et at, "Fundamentals of Powder Diffraction and Structural Characterization of Materials," Springer Science+Business Media, Inc., New York, 2005. Other techniques that may be useful in determining pore sizes (e.g., zeolite pore sizes) include, for example, helium pycnometry or low-pressure argon adsorption techniques. These and other techniques are described in Magee, J. S. et at, "Fluid Catalytic Cracking: Science and Technology," Elsevier Publishing Company, Jul. 1, 1993, pp. 185-195. Pore sizes of mesoporous catalysts may be determined using, for example, nitrogen adsorption techniques, as described in Gregg, S. J. at al, "Adsorption, Surface Area and Porosity," 2nd Ed., Academic Press Inc., New York, 1982 and Rouquerol, F. et al, "Adsorption by powders and porous materials. Principles, Methodology and Applications," Academic Press Inc., New York, 1998.

Regeneration Temperature—The catalyst may be regenerated under flowing air gas at elevated temperatures in order to remove heavier hydrocarbons (coke) from the active catalyst structure. The maximum temperature used in this step is referred to as the "regeneration temperature."

Residence Time ($\tau$)—Residence time is the time a species is in the reaction vessel; defined as the volume of the catalyst bed divided by the flow rate (by volume per second) of gases into the reactor. $\tau$=volume of Catalyst bed (m$^3$)/volumetric flow of reactants (m$^3$/s).

Selectivity—The term "selectivity" refers to the amount of production of a particular product (or products) as a percent of all products resulting from a reaction. For example, if 100 grams of products are produced in a reaction and 80 grams of styrene are found in these products, the selectivity to styrene amongst all products is 80/100=80%. Selectivity can be calculated on a mass basis, as in the aforementioned example, or it can be calculated on a molar basis, where the selectivity is calculated by dividing the moles a particular product by the moles of all products.

WHSV—The term WHSV refers to the Weight Hourly Space Velocity and is defined as the weight of reactant fed to a reactor per hour divided by the weight of the catalyst in the reactor Yield—The term "yield" is used herein to refer to the amount of a product flowing out of a reactor divided by the amount of reactant flowing into the reactor, usually expressed as a percentage or fraction. Mass yield is the mass of a particular product divided by the mass of feed used to prepare that product. When unspecified, "%" refers to mass % which is synonymous with weight %. Ideal gas behavior is assumed so that mole % is the same as volume % in the gas phase.

As is standard patent terminology, the term "comprising" means "including" and does not exclude additional components. Any of the inventive aspects described in conjunction with the term "comprising" also include narrower embodiments in which the term "comprising" is replaced by the narrower terms "consisting essentially of" or "consisting of." As used in this specification, the terms "includes" or "including" should not be read as limiting the invention but, rather, listing exemplary components. As is standard terminology, "systems" include to apparatus and materials (such as reactants and products) and conditions within the apparatus.

SUMMARY OF INVENTION

Figure 1:
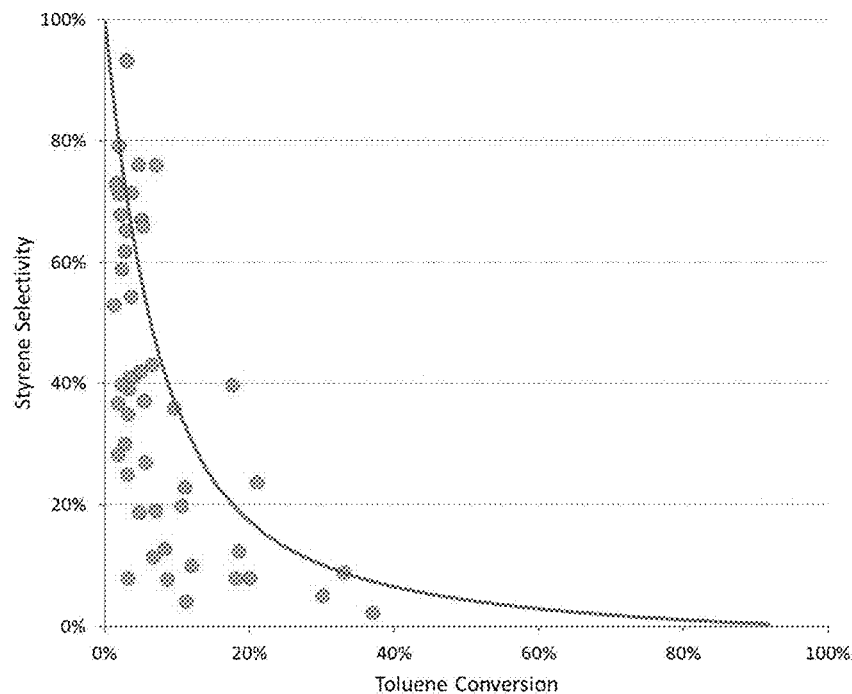
FIG. 1 is a plot of typical catalyst performance from the literature.

Despite decades of research, one major problem that has continued to plague the side-chain alkylation reaction to produce styrene from toluene and methanol (or formaldehyde) is that it does not produce styrene in high enough yields. Highly acidic catalysts produce xylenes while highly basic catalysts produce ethyl-benzene. None of these catalysts produce styrene in yields higher than 4 wt %.

The reason for this phenomenon can be explained as follows—when both styrene and methanol are present in the reactor beyond a threshold value, styrene undergoes catalytic transfer hydrogenation with methanol (or formaldehyde) as the hydrogen donor as follows:

SM+Methanol→EB+CO+H2

As a result, it is next to impossible to cross the 4 wt % styrene yield barrier using either formaldehyde or methanol as the alkylating agent (addition of hydrogen to the reactor feed does not result in styrene hydrogenating to ethylbenzene). In order to improve the selectivity, the issue of competitive adsorption must first be solved. Methanol is a polar molecule (dipole moment=1.69 Debye) and a weak Lewis base that preferentially adsorbs onto soft Lewis acid sites on the catalyst surface. As a non-polar compound (d=0.36 D), toluene adsorbs much less strongly. This "unfair" competition results in a relatively high concentration of methanol on the catalyst surface compared to toluene, resulting in rapid methanol decomposition and low rates of side-chain alkylation. Achieving high selectivity therefore requires altering the adsorption properties of the reactants such that the less reactive species (toluene) is adsorbed more strongly, while the more reactive species (methanol) is present in minority amounts on the catalyst surface. Methanol can be altered to reduce its adsorption relative to toluene while simultaneously reducing its reactivity, and thereby improve the selectivity. This is achieved by converting methanol to dimethyl ether (DME). Being less polar, DME does not compete as vigorously with toluene for catalyst sites and is also less prone to decomposition over a basic catalyst.

Researchers at Exelus substituted DME as the alkylating agent and found out that it worked just as well as methanol and formaldehyde. The reaction side-chain reaction mechanism when using DME as the alkylating agent has not been discussed in literature. Based on analysis of the reactor effluent, it is clear that DME does not first form methanol before reacting with toluene. The reaction effluent shows a only small amount of methanol indicating that it reacts directly. However, the main advantage when using DME is that dimethyl ether does not promote the catalytic transfer hydrogenation reaction helping to keep the styrene molecules intact. As a result, high yields of toluene are possible without sacrificing product selectivity.

Another aspect recognized in our method is the reversibility of the toluene alkylation

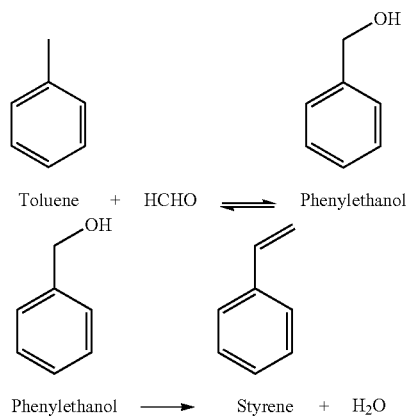

reaction which occurs as shown. For toluene to react in any meaningful amount (conversion>15%), formaldehyde has to be present in excess such that feed HCHO: Toluene>5 mol/mol—which for reasons described above will lead to instant decomposition of HCHO to CO and $H_2$. Using high DME:Toluene feed ratios>5 allows one to achieve meaningful toluene conversions without the problem of quick decomposition of the alkylating agent. The ExSyM process is predicated on three main innovations to overcome this challenge.

Catalyst challenges: Though the use of DME as an alkylating agent reduces some of the challenges associated with the side-chain alkylation of toluene with methanol, there are still catalyst and process challenges that need to be overcome.

Formation of ethylbenzene: Strong basic sites are required for the methyl group activation of toluene. However, very strong basic sites would also promote the transfer hydrogenation between DME and styrene. As mentioned in the mechanism section, there are different routes to form ethylbenzene from toluene i.e., either directly or through styrene as an intermediate. Exelus has found that the rate of formation of ethylbenzene has been found to be much lower when DME was used as the alkylating agent instead of methanol. However, the formation of ethylbenzene was still significant and was needed to be addressed via catalyst modification.

Decomposition of DME: As mentioned earlier, strong base sites that are active for side-chain alkylation also catalyze the undesired methanol decomposition reaction at much higher rates. When DME is used as the alkylating agent, the rate of decomposition to form CO is reduced significantly (from 80% to 20% ??) due to its lower adsorption on catalyst surface. However, Exelus has found that the rate of decomposition reaction is still high. The basicity of the catalyst needs to be tempered to reduce the formation of CO and increase the utilization efficiency of DME.

Product inhibition: The side-chain alkylation reaction is product inhibited, most seriously by styrene. As a result, the reaction rate falls by orders of magnitude as the reaction proceeds and there is more formation of styrene, keeping toluene conversion low (ref). One way to push the reaction forward is by adding excess DME which leads to a gain in toluene conversion because of competitive adsorption between DME and styrene. However, excess DME on surface either leads to DME decomposition resulting in low selectivity or leads to increased transfer hydrogenation of styrene leading to ethylbenzene formation. Additionally, the cost to recycle unreacted DME is prohibitive on a commercial scale. However, the adsorption of styrene on the catalyst reduces when the surface Bronsted acidity is decreased. Hence the product inhibition can be reduced by reducing surface acidity and increasing basicity.

Catalyst deactivation: The catalytic activity usually decreases with time-on-stream due to aromatic coke formation causing pore blockage as evidenced by a reduction in BET surface area (Jiang et al.). This form of deactivation is reversible and can be regenerated by calcination in air. However, the steam that is generated during regeneration or water molecules formed as a by-product during the reaction results in dealumination of the catalyst causing structural damage, reduced crystallinity and a gradual permanent deactivation. Faujasites like X and Y are more susceptible to dealumination due to their lower silica-alumina ratio (SAR) when compared to other zeolites. When DME is used instead of methanol as the alkylating agent, the water content in the feed reduces resulting in lower dealumination during reaction and hence higher long-term catalyst stability. By changing the acid-base properties of the catalyst, coking and consequently water formation during regeneration also can be reduced further leading to increased catalyst stability and regenerability.

Figure 2:
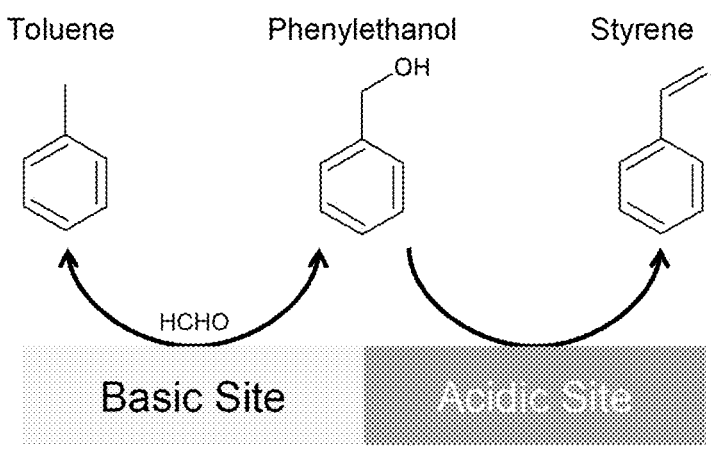
FIG. 2 is a schematic illustration of the catalyst design.

An aspect of the ExSym technology centers around the design of the catalyst sites. Production of 2-phenyl ethanol (PE) the intermediate product from the side-chain alkylation of toluene and HCHO is catalyzed by basic sites while the dehydration of PE is catalyzed by acid sites. This aspect of the catalyst design is illustrated in the FIG. 2.

The rate of PE and Styrene Monomer (SM) formation can thus be written as follows $$d[PE]/dt = k_1 n_B S_B [\text{Toluene}][HCHO]$$

$$d[SM]/dt = k_2 n_A S_A [PE]$$

where $k_i$ is the rate constant, n refers to the number of sites, s to the strength of sites and the subscripts A and B refer to Acidic and Basic sites. The number of sites and the strengths of sites have to be carefully optimized to ensure adequate catalyst activity as well as product selectivity. A balanced combination of strong and weak basic sites along with acid sites for dehydration of phenylethanol is thus desirable for a high yield of styrene.

As discussed in literature, basicity was proven to be a crucial factor for the reaction which activates the methyl group of toluene. A catalyst with predominantly acid sites leads to ring-alkylation leading to formation of xylenes and reduced side-chain alkylation. Exelus found that addition of strong electropositive ions either via ion-exchange or impregnation increased the basicity of the catalyst resulting in increased side-chain alkylation activity of toluene with DME. A synergistic role of ion clusters and ions resulted in increasing both the base strength as well as the number of base sites. However, making a catalyst with just basic sites led to high formation of EB and increased decomposition of DME.

Introduction of transition metals either independently or in conjunction with Boron and/or Phosphorus introduced weak Lewis acidity which resulted in fast dehydration of phenylethanol to form styrene. At the same time, the addition of modifiers reduced the strength and number of excess base sites which suppressed both the decomposition of DME to form CO and also the formation of ethylbenzene. A careful balance of surface acid-base properties also ensured reduced product inhibition by styrene resulting in longer reaction times and lower formation of water during regeneration. The reduced coking obtained by reducing surface acidity along with the addition of rare-earth elements resulted in reduced dealumination leading to increased long-term stability.

Two main factors influence the design of the ExSyM reactor a) reaction endotherm which leads to a drop in temperature and b) catalyst deactivation which leads to a drop in catalyst activity.

Reaction Endotherm: Toluene+DME→Styrene ΔH=56 kJ/mole

Catalyst Coking: Styrene+n DME→Coke

Though the reaction endotherm is roughly half of the ethylbenzene dehydrogenation reaction of about 56 kJ/mole, it results in a substantial reduction in reaction temperature if the reactor operated adiabatically. A method for adding heat to the reactor is required. In addition, formation of styrene leads to coking of the catalyst. As a result, the catalyst activity drops as a function of time and has to be periodically regenerated. In a conventional ethylbenzene dehydrogenation reactor, steam is used to overcome both these issues. Steam supplies the heat of reaction while also removing coke from the catalyst which allows the active sites to maintain acceptable levels of activity. However, large amounts of steam reform methanol or dimethyl ether and thus cannot be used in the side-chain alkylation reaction process. These two critical factors are the major drivers of reactor design for most paraffin dehydrogenation technologies as well as the side-chain alkylation process. To design an effective reactive system for ExSyM, it is helpful to understand the concepts used to design reactor designs used for dehydrogenation processes. Dehydrogenation reactors fall into two main groups:

Cyclic Fixed-Bed Reactors: In this configuration, the reaction is typically run adiabatically in a fixed bed configuration for a few minutes to ensure acceptable catalyst activity over the entire cycle. The hydrocarbons are then purged using an inert gas such as steam and then the catalyst regenerated using air. The regeneration step serves two purposes. It removes the coke from the catalyst thereby restoring catalyst activity. The air oxidation of coke hydrocarbons reheats the catalyst body. This heat serves to supply energy to the reaction endotherm during the reaction cycle. Several reactors are used in this configuration so that while some reactors are in the reaction mode others are either in the regeneration or purge mode. Operation of these reactors are complex due to valving issues but scale-up is relatively straight forward.

Continuously regenerated catalytic reactors: In this configuration, the catalyst is continuously flowing between the reactor (where the dehydrogenation reaction occurs) and the regenerator (where coke on the active sites are removed either by hydrogenation or combustion). The reaction takes place adiabatically and the reaction endotherm is supplied either by the heated catalyst after regeneration or by interstage heaters. Some technologies use a radial flow reactor to minimize pressure drop across the catalyst bed while others use FCC-type riser reactors to keep coke formation in check. Two factors make these reactors configuration attractive for dehydrogenation reactions. A single reactor and regenerator is used in this configuration eliminating the need for expensive fired heaters to supply heat to the reaction endotherm allowing cost-effective designs. By keeping the reaction cycle to a few seconds long, minimizes the amount of coke formed on the catalyst. This helps to minimize by-product formation reducing raw material consumption and hence operating costs.

Given the constraints of the SCA reaction, a fluidized riser reactor with regenerator was chosen as the ideal candidate for the ExSyM process. The riser reactor design equations can be written as $$t=z/U_G$$

$$A_t/A_o=e^{(-kD\ t)}$$

$$dn/dt=k\ A_t[DME][\text{Toluene}]/(1+K[\text{Styrene}])$$

$$\delta T=n\Delta H/m\ C_P$$

where t refers to gas phase residence time, z, the length along the riser, UG the gas superficial velocity, $A_t$ and $A_0$ number of active sites at time t=t and t=0, kD the deactivation rate constant, n the moles of toluene reacted, δT the temperature drop, DH the heat of reaction, m the mass of catalyst and CP the heat capacity of catalyst.

Figure 3:
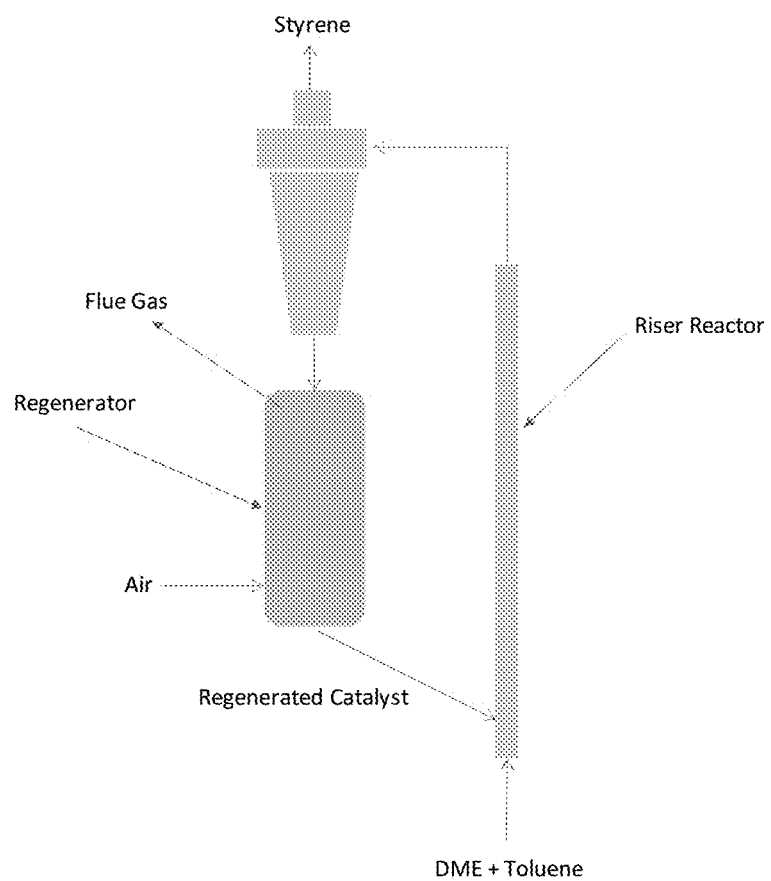
FIG. 3 schematically illustrates a reactor design suitable for the invention.
Figure 4:
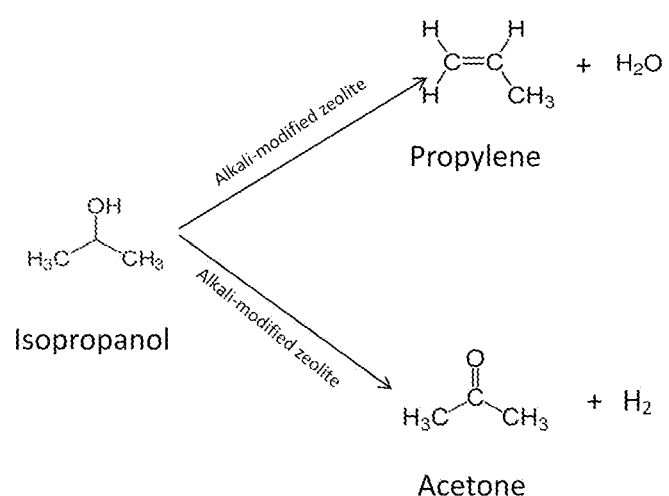
FIG. 4 shows a probe reaction to quantify Basic to Acidic Sites ratio.

This design achieves two objectives. It limits the adiabatic temperature drop δT<20° C. and it provides for a continuous stream of fresh catalyst to the reaction zone so that $A_t/A_0$>0.9. The residence time in the riser varies between 1-3 seconds while time in the regenerator is around 15-30 minutes. FIG. 3 shows a FCC-type reactor design for the ExSyM Process.

Preheated hydrocarbon feed is fed to the inlet of the riser reactor. Hot catalyst coming from a catalyst surge vessel and catalyst regenerator is mixed and fluidized by the feed vapor at the riser inlet. The feed and catalyst flow upward in the riser reactor in a co-current flow. As the feed and catalyst pass upward through the riser reactor, dehydrogenation takes place, consuming heat and producing hydrogen. The toluene conversion is limited to 20-25% to minimize by-product formation as well as control the reaction endotherm. This allows the exit temperature in the riser reactor to be maintained to within 20-25° C. of the inlet temperature. The riser effluent is routed from the riser reactor outlet to a cyclone, where gas/solid separation is done. The solid catalyst collected from the bottom of the separator is sent to a hot surge vessel, while the product gas is sent to from the top of the cyclone to a vapor cooler. The cooled vapor is sent to a water/hydrocarbon separator where water is collected at the bottom and hydrogen and hydrocarbons are collected from the top. The hydrocarbon vapors are compressed and sent for further separation as done in conventional dehydrogenation processes.

The coked catalyst is stripped of volatiles with steam, in a catalyst stripper and the stripped catalyst is then regenerated. The catalyst regenerator burns coke from the catalyst with air. This heated catalyst is recycled to the riser reactor. Flue gas formed by burning coke in the regenerator is treated for removal of particulates and for conversion of carbon monoxide, after which the flue gas is normally discharged into the atmosphere. The ExSyM regenerator uses a fast fluidized bed coke combustor, a dilute phase transport riser mounted above the coke combustor, and a second dense bed, for collection of regenerated catalyst for recycle to the reactor and frequently for recycle to the coke combustor as well. Such regenerators are now widely used, because they allow FCC units to operate with roughly half the catalyst required when using a prior art, bubbling dense bed regenerator.

In a preferred aspect, the invention provides a method of producing styrene from a feed comprising of methanol and toluene. The process comprises the following steps
1) Converting methanol to di-methyl ether (DME) over an acid catalyst
2) Converting DME and toluene to styrene adiabatically over a bi-functional catalyst characterizable by
   a. Activity Parameter>0.02
   b. Selectivity Parameter>0.1 and
   c. Stability parameter<0.005 wherein the parameters are characterizable by a test where the bi-functional catalyst is loaded in a fixed-bed reactor such that the 50>dT/dP>10 (diameter of tube to diameter of catalyst particles) and 200>L/dP>50 (length of catalyst bed to diameter of catalyst particles) and 2>dP>0.5 mm exposed to a feed stream comprising of DME and toluene at a ratio of 5 mol/mol at a temperature of 425° C., atmospheric pressure and a feed rate of 50 hr$^{-1}$ weight hourly space velocity.

Activity Parameter—To compare the catalyst performance under different conditions, the activity is quantified by the activity parameter which is the reaction rate constant described above for the side-chain alkylation reaction given below:

Activity Parameter (AP) is calculated from conversion (x) and WHSV as follows $$AP(k)=WHSV*-\ln(1-x)$$

A catalyst converting toluene with a high activity will have an activity parameter>0.02.

Selectivity Parameter—Since selectivity of styrene monomer (SM) varies with toluene conversion, a method is required to compare selectivity obtained by different catalysts under various conversions. Selectivity parameter is calculated from the ratio of the first-order rate constant of the toluene conversion to SM (k1) to the first-order rate constant of the styrene conversion to ethyl benzene (EB) (k2) and remains constant irrespective of the toluene conversion for a successive reaction given below:

A catalyst producing styrene monomer with a high selectivity will have a selectivity parameter>0.1.

The selectivity parameter (SP) (=k1/k2) is calculated from toluene conversion (x) and SM yield (y) by solving the equations shown below:

$$k1=WHSV*-\ln(1-x)$$

$$y=[k1/(k2-k1)][e^{(-k1/WHSV)}-e^{(-k2/WHSV)}]$$

In one aspect, the invention provides a method of producing styrene from a feed comprising of methanol and toluene at a molar feed ratio of 0.1 to 10, reaction temperature of 300-600° C., a space velocity of 0.1-25 hr$^{-1}$ or 0.1-15 hr$^{-1}$ and a pressure of 0.01-0.2 MPa for a reaction period in the range of 0.05 seconds to 10 hours over a bi-functional catalyst, and regenerating the said catalyst with an oxygen-containing gas wherein said catalyst regeneration is performed at a temperature of 300-600° C., a pressure of 0.01-0.2 MPa and a regeneration period ranging from 0.05 seconds to 10 hours.

In some preferred embodiments, the contacting step is carried out in a fluidized bed reactor or a fixed-bed swing reactor.

In some preferred embodiments, the invention provides advantages such as: the product of the catalyst activity and catalyst selectivity exceeding 0.1 ton of product per hour per ton of catalyst; and the overall catalyst consumption does not exceed 1 kg of catalyst per ton of product.

In another aspect, the invention provides a method of producing styrene, comprising: passing dimethyl-ether (DME) into a reaction chamber; passing toluene into the reaction chamber; wherein the reactor comprises a zeolite catalyst having a Si to Al molar ratio of approximately 1 to 10, and is preferably either zeolite X or zeolite Y wherein 50-80% of the exchangeable sodium in the zeolite is replaced by Group 1 alkali metal salts of potassium, rubidium or cesium and contains at least 0.1 wt % or at least 0.2 wt % or in the range of 0.1 to 1 wt % B. The DME and the toluene in the reaction chamber react in the presence of the catalyst to make styrene under steady state conditions.

The invention can be further characterized by one or any combination of the following optional features: wherein the catalyst has a surface area density of between approximately 300-500 m$^2$/g and BET surface area of approximately 600 m$^2$/gm; wherein the catalyst has an AP of at least 0.02, or at least 0.04, or at least 0.05, or at least 0.07, or in the range of 0.02 to 0.10 or 0.09 and/or a SP of at least 0.1, or at least 0.2, or at least 0.3, or in the range of 0.1 to 0.5 or 0.4; where the reaction chamber is where the reaction is adiabatic or nearly adiabatic; wherein the reaction chamber comprises a temperature in the range 300 and 600° C., preferably 400 and 550° C.; wherein the step of reacting is conducted at a pressure between 1 atm and 10 atm; wherein the reactants (DME and toluene) flows into the reaction chamber at a toluene WHSV between 0.1 and 10.0 hr$^{-1}$; wherein the feed toluene comprises a mixture of benzene and toluene; conducted at a feed DME to Toluene ratio of 1.0 to 100 mol/mol, preferably 5-20 mol/mol; wherein the toluene feed comprises at least 90 mol % toluene; where the styrene selectivity>50 mol %; where the EB selectivity<50 mol %; where the toluene conversion>10%; where the reaction chamber comprises a fixed-bed catalyst; further comprises regenerating the catalyst in flowing air at a temperature of at least 300° C. and a GHSV of at least 500; wherein the catalyst is regenerated in flowing oxygen at a temperature of at least 300° C. and a GHSV of at least 500; wherein the method is run continuously for a period>6 hours without regenerating the catalyst.

In another aspect, the invention provides a catalyst for producing styrene from DME and toluene, comprising: zeolite X or zeolite Y wherein 50% of the exchangeable sodium in the zeolite is replaced by Group 1 alkali metal salts of potassium, rubidium or cesium and containing at least 0.1 wt % or at least 0.2 wt % or in the range of 0.1 to 1 wt % B.

In another aspect, the invention provides a catalyst for producing styrene from DME and toluene, comprising: zeolite X or zeolite Y, comprising potassium, rubidium or cesium and containing at least 0.1 wt % or at least 0.2 wt % or in the range of 0.1 to 1 wt % B; and wherein the catalyst is characterizable by
  a. Activity Parameter>0.02
  b. Selectivity Parameter>0.1 and
  c. Stability parameter<0.005
  using a test where the catalyst is loaded in a fixed-bed reactor such that the 50>dT/dP>10 (diameter of tube to diameter of catalyst particles) and 200>L/dP>50 (length of catalyst bed to diameter of catalyst particles) and 2>dP>0.5 mm exposed to a feed stream comprising of DME and Toluene at a ratio of 5 mol/mol at a temperature of 425° C., atmospheric pressure and a feed rate of 50 hr$^{-1}$ weight hourly space velocity.

The invention can be further characterized by one or any combination of the following optional features: wherein the catalyst that is preferably a zeolite which has a Si to Al molar ratio of approximately 1 to 10, and is preferably either zeolite X or zeolite Y having a surface area density of between approximately 400 m$^2$/g and approximately 600 m$^2$/g; wherein the catalyst is characterizable by
  d. Activity Parameter>0.02
  e. Selectivity Parameter>0.1 and
  f. Stability parameter<0.005
  using a test where the catalyst is loaded in a fixed-bed reactor such that the 50>dT/dP>10 (diameter of tube to diameter of catalyst particles) and 200>L/dP>50 (length of catalyst bed to diameter of catalyst particles) and 2>dP>0.5 mm exposed to a feed stream comprising of DME and Toluene at a ratio of 5 mol/mol at a temperature of 425° C., atmospheric pressure and a feed rate of 50 hr$^{-1}$ weight hourly space velocity; wherein the anions of the alkali metal salt anions are chosen from hydroxide, acetate, tetraborate, pentaborate, tungstate, carbonate, titanate or phosphate; wherein the molar ratio of the alkali cation to the residual sodium cation is greater than 1.0; wherein the ratio of 20>Basic/Acid (BAR) sites>1; and/or wherein the boric acid loading varies from 0.5 to 5 wt %.

In another aspect, the invention provides a method for making styrene comprising: generating DME by dehydration of methanol, providing a reaction zone containing a catalyst comprising a bi-functional zeolite for reacting toluene and DME to form styrene; providing feed-streams of toluene and DME to the reaction zone; reacting toluene and DME in the reaction zone containing the catalyst at a temperature between 300 to 500° C. and preferably a pressure between 1 atm to 10 atm to form a first product stream comprising styrene and water; at least partially separating the product stream to form a styrene product stream; removing unreacted toluene from the first product stream and recycling unreacted toluene to the reaction zone.

In another aspect, the invention comprises a method of making a catalyst, comprising: providing a zeolite comprising zeolite X or zeolite Y having a Si/Al ratio in the range of 1.0 to 10; conducting an ion exchange with K, Rb, or Cs to remove 50-80% of Na; impregnating the resulting zeolite with 0.5 to 5 wt % boric acid (based on the weight of zeolite); and drying. In various embodiments, the resulting catalyst may have any of the characteristics described herein.

In another aspect, the invention provides a method of making an alkylation catalyst, comprising a zeolite which has a Si to Al molar ratio of approximately 1 to 10, and is preferably either zeolite X or zeolite Y having a surface area density of between approximately 400 m$^2$/g and approximately 600 m$^2$/g characterizable by a Basic Site/Acidic Site ratio (BAR) between 1 and 20.

The zeolite is ion-exchanged with Group 1 alkali metal salts of potassium, rubidium or cesium with anions comprising of either hydroxide or carbonate or phosphate or tetraborate or pentaborate or acetate, or titanate to replace at least 50% of the exchangeable sodium in the zeolite composition. The ion-exchanged zeolite is then impregnated with boric acid such that the loading of boric acid on the zeolite exceeds 0.75 wt %. To produce styrene with high catalyst activity (AP>0.02) and adequate product selectivity (SP>0.1) the number of sites and the strengths of sites have to be carefully optimized. The performance of the catalyst can be modified by controlling the ratio of basic sites to the acidic sites (BAR) for the side-chain alkylation of toluene.

A probe reaction is used to quantify the ratio of basic sites to acidic sites (BAR). When isopropanol is passed over an acid-base catalyst, it is generally agreed that the formation of acetone via a dehydrogenation pathway occurs over basic sites whereas formation of propylene via dehydration pathway occurs over acid sites. Therefore, depending upon the outcome of products, catalysts can be characterized as basic, acidic, or a combination of both in certain proportion. The selectivity to acetone will hence be proportional to Basic Sites while the selectivity to propylene will be proportional to Acid Sites.

An effective SCA catalyst will have a ratio of 20>Basic/Acid (BAR) sites>1 using a test where the bi-functional catalyst is loaded in a fixed-bed reactor such that the 50>dT/dP>10 (diameter of tube to diameter of catalyst particles) and 200>L/dP>50 (length of catalyst bed to diameter of catalyst particles) and 2>dP>0.5 mm exposed to a feed stream comprising of isopropanol and air at a temperature of 375° C., atmospheric pressure and a isopropanol flow rate of 50 hr$^{-1}$ weight hourly space velocity.

For instance, at a reaction temperature of T=375° C. (648 K), 1% isopropanol in air (vol/vol), and isopropanol WHSV=150/hour, for an isopropanol conversion of x=10% and acetone selectivity=90%, we calculate the BAR for Catalyst C:

$$\text{Basic sites to the acidic sites (BAR)}=9$$

The invention is further elucidated in the examples below. In some preferred embodiments, the invention may be further characterized by any selected descriptions from the examples, for example, within ±20% (or within ±10%) of any of the values in any of the examples, tables or figures; however, the scope of the present invention, in its broader aspects, is not intended to be limited by these examples.

EXAMPLE 1

The starting material was a commercial zeolite X having a SiO2/Al2O3 molar ratio of 2.8 (Si/Al of 1.4) and a sodium content of 15% by weight. 15 grams of the zeolite powder was suspended in 250 mL of deionized water and stirred for 30 minutes after which the solution was vacuum filtered using a Buchner filter, a filter flask and a filter paper.

A potassium ion exchange was performed after the initial water wash. The zeolite was suspended in 250 mL of a 0.4 M KOH solution and heated to 80° C. while stirring for 2 hours. The KOH solution was then filtered out and replaced with a fresh solution. This ion-exchange procedure was repeated two more times. After filtering the solution, the zeolite was left to dry at room temperature.

Following the potassium exchange, the zeolite was impregnated with Boric acid (1 wt %) using the incipient wetness procedure described below. Initially, 0.15 g of Boric acid was dissolved in 10 g of methanol. This solution was then added dropwise to 15 g of catalyst and the resulting mixture was left in a covered beaker. After 4 hours, the cover was removed and the zeolite was dried slowly at room temperature for 16 hours. The catalyst was then dried in a low temperature oven at 80° C. for 4 hours following which it was pelletized, crushed and sieved to yield particles with a size range of 0.5 mm to 1.4 mm.

This catalyst is designated as Catalyst A

EXAMPLE 2

The catalyst was prepared as in Example 1 with the difference being that the base cation of hydroxide salt used for ion exchange was sodium.

This catalyst is designated as Catalyst B

EXAMPLE 3

The catalyst was prepared as in Example 1 with the difference being that the base cation of hydroxide salt used for ion exchange was cesium.

This catalyst is designated as Catalyst C

EXAMPLE 4

The catalyst was prepared as in Example 1 with the difference being that the base cation of hydroxide salt used for ion exchange was lithium.

This catalyst is designated as Catalyst D

EXAMPLE 5

The catalyst was prepared as in Example 1 with the difference being that the base cation of hydroxide salt used for ion exchange was barium.

This catalyst is designated as Catalyst E

EXAMPLE 6

The catalyst was prepared as in Example 1 with the difference being that the salt used for ion exchange was potassium nitrate.

This catalyst is designated as Catalyst F

EXAMPLE 7

The catalyst was prepared as in Example 1 with the difference being that the salt used for ion exchange was potassium tetra-borate.

This catalyst is designated as Catalyst G

EXAMPLE 8

The catalyst was prepared as in Example 1 with the difference being that the salt used for ion exchange was potassium penta-borate.

This catalyst is designated as Catalyst H

EXAMPLE 9

The catalyst was prepared as in Example 1 with the difference being that the salt used for ion exchange was potassium chloride.

This catalyst is designated as Catalyst I

EXAMPLE 10

The catalyst was prepared as in Example 1 with the difference being that the salt used for ion exchange was potassium acetate.

This catalyst is designated as Catalyst J

EXAMPLE 11

The catalyst was prepared as in Example 1 with the difference being that the concentration of cesium hydroxide salt used for ion exchange was 0.2 M.

This catalyst is designated as Catalyst K

EXAMPLE 12

The catalyst was prepared as in Example 1 with the difference being that the concentration of cesium hydroxide salt used for ion exchange was 0.5 M.

This catalyst is designated as Catalyst L

EXAMPLE 13

The catalyst was prepared as in Example 1 with the difference being that the concentration of cesium hydroxide salt used for ion exchange was 0.15 M.

This catalyst is designated as Catalyst M

EXAMPLE 14

The catalyst was prepared as in Example 1 with the difference being that the concentration of cesium hydroxide salt used for ion exchange was 0.3 M.

This catalyst is designated as Catalyst N

EXAMPLE 15

The catalyst was prepared as in Example 1 with the difference being that the starting material was a commercial zeolite NaY having a SiO2/Al2O3 molar ratio of 5 (Si/Al of 2.5) and a sodium content of 13% by weight.

This catalyst is designated as Catalyst O

EXAMPLE 16

The catalyst was prepared as in Example 1 with the difference being that the starting material was a 1 to 1 mixture of commercial zeolite NaX having a SiO2/Al2O3 molar ratio of 2.8 (Si/Al of 1.4) and a sodium content of 15% by weight and TiO2.

This catalyst is designated as Catalyst P

EXAMPLE 17

The catalyst was prepared as in Example 1 with the difference being that the starting material was a 1 to 1 mixture of commercial zeolites NaX having a SiO2/Al2O3 molar ratio of 2.8 (Si/Al of 1.4) and a sodium content of 15% by weight and NaY having a SiO2/Al2O3 molar ratio of 5 (Si/Al of 2.5) and a sodium content of 13% by weight.

This catalyst is designated as Catalyst Q

EXAMPLE 18

The starting material was a commercial hydrotalcite as a support. A potassium ion was added to the 15 grams of support via incipient wetness technique of impregnation.

Potassium hydroxide precursor having 1 wt % potassium was dissolved in 10 ml of DI water and added to the support drop-wise to wet the support. After impregnation, the zeolite was left to dry at room temperature.

Following the potassium addition, the hydrotalcite was impregnated with Boric acid (1 wt %) using the incipient wetness procedure described below. Initially, 0.15 g of Boric acid was dissolved in 10 g of methanol. This solution was then added drop-wise to 15 g of catalyst and the resulting mixture was left in a covered beaker. After 4 hours, the cover was removed and the zeolite was dried slowly at room temperature for 16 hours. The catalyst was then dried in a low temperature oven at 80° C. for 4 hours following which it was pelletized, crushed and sieved to yield particles with a size range of 0.5 mm to 1.4 mm.

This catalyst is designated as Catalyst R

EXAMPLE 19

The starting material was a commercial zeolite X having a SiO2/Al2O3 molar ratio of 2.8 (Si/Al of 1.4) and a sodium content of 15% by weight. 15 grams of the zeolite powder was suspended in 250 mL of deionized water and stirred for 30 minutes after which the solution was vacuum filtered using a Buchner filter, a filter flask and a filter paper.

A potassium ion exchange was performed after the initial water wash. The zeolite was suspended in 250 mL of a 0.2 M KOH solution and heated to 80° C. while stirring for 2 hours. The potassium solution was then filtered out and replaced with a fresh solution. This ion-exchange procedure was repeated two more times. After filtering the solution, the zeolite was left to dry at room temperature. After drying, more potassium ion was added to the support via incipient wetness technique of impregnation. Potassium hydroxide precursor having 0.56 wt % potassium was dissolved in 10 ml of DI water and added to the support drop-wise to wet the support. After impregnation, the zeolite was dried at room temperature.

Following the potassium addition, the zeolite was impregnated with Boric acid (1 wt %) using the incipient wetness procedure described below. Initially, 0.15 g of Boric acid was dissolved in 10 g of methanol. This solution was then added drop-wise to 15 g of catalyst and the resulting mixture was left in a covered beaker. After 4 hours, the cover was removed and the zeolite was dried slowly at room temperature for 16 hours. The catalyst was then dried in a low temperature oven at 80° C. for 4 hours following which it was pelletized, crushed and sieved to yield particles with a size range of 0.5 mm to 1.4 mm.

This catalyst is designated as Catalyst S

EXAMPLE 20

The starting material was a commercial zeolite X having a SiO2/Al2O3 molar ratio of 2.8 (Si/Al of 1.4) and a sodium content of 15% by weight. 15 grams of the zeolite powder was suspended in 250 mL of deionized water and stirred for 30 minutes after which the solution was vacuum filtered using a Buchner filter, a filter flask and a filter paper.

A cesium ion exchange was performed after the initial water wash. The zeolite was suspended in 250 mL of a 0.4 M CsOH solution and heated to 80° C. while stirring for 2 hours. The CsOH solution was then filtered out and replaced with a fresh solution. This ion-exchange procedure was repeated two more times. After filtering the solution, the zeolite was left to dry at room temperature.

Following the cesium exchange, the zeolite was impregnated with 1 wt % Boric acid using the incipient wetness procedure described below. Initially, 0.15 g of Boric acid was dissolved in 10 g of methanol. This solution was then added dropwise to 15 g of catalyst and the resulting mixture was left in a covered beaker. After 4 hours, the cover was removed and the zeolite was dried slowly at room temperature for 16 hours. The catalyst was then dried in a low temperature oven at 80° C. for 4 hours following which it was pelletized, crushed and sieved to yield particles with a size range of 0.5 mm to 1.4 mm.

This catalyst is designated as Catalyst T.

EXAMPLE 21

The catalyst was prepared as in Example 20 with the difference being that after the cesium ion exchange, the amount of boric acid added to the support via impregnation was 3.0 wt %.

This catalyst is designated as Catalyst U

EXAMPLE 22

The catalyst was prepared as in Example 20 with the difference being that after the cesium ion exchange, the amount of boric acid added to the support via impregnation was 5.0 wt %.

This catalyst is designated as Catalyst V

EXAMPLE 23

The catalyst was prepared as in Example 20 with the difference being that after the cesium ion exchange, the amount of boric acid added to the support via impregnation was 10.0 wt %.

This catalyst is designated as Catalyst W

EXAMPLE 24

The catalyst was prepared as in Example 20 with the difference being that after the cesium ion exchange, the amount of boric acid added to the support via impregnation was 0.0 wt %.

This catalyst is designated as Catalyst X

EXAMPLE 25

The catalyst was prepared as in Example 1 with the difference being that before pelletizing; the catalyst was dry mixed with NaY with catalyst to NaY ratio of 4 to 1 by weight.

This catalyst is designated as Catalyst Y

EXAMPLE 26

The catalyst was prepared as in Example 1 with the difference being that before pelletizing; the catalyst was dry mixed with ZSM-5 with catalyst to ZSM-5 ratio of 4 to 1 by weight.

This catalyst is designated as Catalyst Z

EXAMPLE 27

The catalyst was prepared as in Example 1 with the difference being that before pelletizing; the catalyst was dry mixed with NH4Y with catalyst to NH4Y ratio of 4 to 1 by weight.

This catalyst is designated as Catalyst AA.

EXAMPLE 28

The catalyst was prepared as in Example 1 with the difference being that before pelletizing; the catalyst was dry mixed with silica-alumina with catalyst to silica-alumina ratio of 4 to 1 by weight.
This catalyst is designated as Catalyst AB.

EXAMPLE 29

The catalyst was prepared as in Example 1 with the difference being that before pelletizing; the catalyst was dry mixed with silica with catalyst to silica ratio of 4 to 1 by weight.
This catalyst is designated as Catalyst AC.

EXAMPLE 30

The catalyst was prepared as in Example 1 with the difference being that before pelletizing; the catalyst was dry mixed with alumina with catalyst to alumina ratio of 4 to 1 by weight.
This catalyst is designated as Catalyst AD.

EXAMPLE 31

The catalyst was prepared as in Example 1 with the difference being that before pelletizing; the catalyst was dry mixed with titania with catalyst to titania ratio of 4 to 1 by weight.
This catalyst is designated as Catalyst AE.

EXAMPLE 32

The catalyst was prepared as in Example 1 with the difference being that before pelletizing; the catalyst was dry mixed with catalyst to titanium silicalite-1 ratio of 4 to 1 by weight.
This catalyst is designated as Catalyst AF.

EXAMPLE 33

The catalyst was prepared as in Example 1 with the difference being that following the potassium exchange, the zeolite was impregnated with potassium tetraborate instead of boric acid.
This catalyst is designated as Catalyst AG.

EXAMPLE 34

The catalyst was prepared as in Example 1 with the difference being that following the potassium exchange, the zeolite was impregnated with zinc borate instead of boric acid.
This catalyst is designated as Catalyst AH.

EXAMPLE 35

The catalyst was prepared as in Example 1 with the difference being that following the potassium exchange, the zeolite was impregnated with phosphoric acid instead of boric acid.
This catalyst is designated as Catalyst AI.

EXAMPLE 36

The catalyst was prepared as in Example 1 with the difference being that following the potassium exchange, the zeolite was impregnated with potassium phosphate instead of boric acid.
This catalyst is designated as Catalyst AJ.

EXAMPLE 37

The catalyst was prepared as in Example 1 with the difference being that following the potassium exchange, the zeolite was impregnated with potassium pentaborate instead of boric acid.
This catalyst is designated as Catalyst AK.

EXAMPLE 38

The catalyst was prepared as in Example 1 with the difference being that before pelletizing; 1 wt % zinc in the form of zinc nitrate was added to the catalyst and dried.
This catalyst is designated as Catalyst AL.

EXAMPLE 39

The catalyst was prepared as in Example 1 with the difference being that before pelletizing; 1 wt % zirconium in the form of zirconium nitrate was added to the catalyst and dried.
This catalyst is designated as Catalyst AM

EXAMPLE 40

The catalyst was prepared as in Example 1 with the difference being that before pelletizing; 2 wt % copper in the form of copper nitrate was added to the catalyst and dried.
This catalyst is designated as Catalyst AN.

EXAMPLE 41

The catalyst was prepared as in Example 1 with the difference being that before pelletizing; 1 wt % silver in the form of silver nitrate was added to the catalyst and dried.
This catalyst is designated as Catalyst AO.

EXAMPLE 42

The catalyst was prepared as in Example 1 with the difference being that before pelletizing; 3 wt % aluminum in the form of aluminum nitrate was added to the catalyst and dried.
This catalyst is designated as Catalyst AP.

EXAMPLE 43

The catalyst was prepared as in Example 1 with the difference being that before pelletizing; 1 wt % lanthanum in the form of lanthanum nitrate was added to the catalyst and dried.
This catalyst is designated as Catalyst AQ.

EXAMPLE 44

The catalyst was prepared as in Example 1 with the difference being that before pelletizing; 1 wt % cerium in the form of cerium nitrate was added to the catalyst and dried.
This catalyst is designated as Catalyst AR.

EXAMPLE 45

Catalyst performance testing was performed using an isothermal packed bed reactor setup. Heating is controlled using an Omega temperature control unit and a ceramic heating element. Toluene (99.9 wt % purity) is pumped into the reactor from a pressurized feed cylinder using a HPLC-style metering pump (Eldex). The flow is measured by monitoring the weight change in the cylinder via an electronic balance. Dimethyl ether (DME) (>99.9 wt % purity) and Nitrogen (which is used as an internal standard) are introduced into the system through mass flow controllers (MFC) (Brooks 5850 E series). Air is also metered through a MFC during regeneration.

An electric furnace equipped with a PID controller is used to maintain the desired reaction temperature. The furnace temperature is measured via thermocouple located adjacent to the reactor. A thermocouple is also installed inside the catalyst bed to monitor the reaction temperature. A preheating zone is used to bring feed to reaction temperature prior to entering the reactor. The reactor effluent is immediately cooled to −10° C. with a chilled bath using an ethylene glycol/water mixture as coolant. A gas/liquid separator is installed at exit to collect both gas and liquid samples for GC analysis.

The catalyst of interest was loaded into reactor such that $dT/dP>10$ and $L/dP>50$ The catalyst was activated in dry air at atmospheric pressure at 425° C. (4 hours). Following activation the reactor was then purged with dry nitrogen. The feed of toluene and DME was then metered in such that the WHSV=50/hr and the DME/Toluene feed ratio was 5 mol/mol. The test was run at 425° C. for 6 hours and the catalyst regenerated using air at 425 C after each run.

REFERENCES

1. James P. Nehlsen, John Young, Mitrajit Mukherjee, The Catalyst Review, 2010, 23 (4), 6-10.
2. Carlo Perego, Patrizia Ingallina, Catalysis Today, 2002, 73, 1-2, 3-22.
3. http://www.chemwinfo.com/private folder/Uploadfiles2015 July/CBI_Technolo gy_Ethylbenzene-Styrene.pdf.
4. J. K. F. Buijink, Jean-Paul Lange, A. N. R. Bos, A. D. Horton, F. G. M. Niele, Chapter 13, Mechanisms in Homogeneous and Heterogeneous Epoxidation Catalysis, 2008, 355-371.
5. V. Wong and S.-H. Wandg, Process Economics Program Review, 1996, 94-2-4.
6. Domenico Sanfilippo, Guido Capone, Alberto Cipelli, Richard Pierce, Howard Clark, Matt Pretz, Stud. Surf. Sci. Cat., 2007, 167, 505-510.
7. https://cen.acs.org/articles/85/i12/Styrene-Breakthrough.html.
8. L. N. Sidorenko, P. N. Galich and V. S. Gutirya, Dokl. Akad. Nauk SSSR, 1967, 173, 132-133.
9. T. Yashima, K. Sato, T. Hayasaka and N. Hara, J. Catal., 1972, 26, 303-312.
10. Zhe Hong, Chuanfang Xiong, Guoqing Zhao, Zhirong Zhu. Catal. Sci. Technol., 2019,9, 6828-6840
11. E. Mielczarski and M. E. Davis, Ind. Eng. Chem. Res., 1990, 29, 1579-1582.
12. A. Philippou and M. W. Anderson, J. Am. Chem. Soc., 1994, 116, 5774-5783.
13. H. Hattori, Appl. Catal., A, 2015, 504, 103-109.
14. J. Jiang, G. Z. Lu, C. X. Miao, X. Wu, W. H. Wu and Q. Sun, Microporous Mesoporous Mater., 2013, 167, 213-220.
15. A. E. Palomares, G. EderMirth and J. A. Lercher, J. Catal., 1997, 168, 442-449.
16. H. Itoh, A. Miyamoto and Y. Murakami, J. Catal., 1980, 64, 284-294.
17. P. D. Li, Q. Han, X. M. Zhang, Y. Y. Yuan, Y. F. Zhang, H. C. Guo, L. Xu and L. Xu, Catal. Sci. Technol., 2018, 8, 3346-3356.
18. B. B. Tope, W. O. Alabi, A. M. Aitani, H. Hattori and S. S. Al-Khattaf, Appl. Catal., A, 2012, 443, 214-220.
19. M. Hunger, U. Schenk and J. Weitkamp, J. Mol. Catal. A: Chem., 1998, 134, 97-109.
20. S. T. King and J. M. Garces, J. Catal., 1987, 104, 59-70.
21. Tawan Sooknoi, John Dwyer, Studies in Surf. Sci. Cat., 1995, 97, 423-429,
22. A. E. Palomares, G. EderMirth and J. A. Lercher, J. Catal., 1997, 168, 442-449.
23. A. E. Palomares, G. Eder-Mirth, M. Rep and J. A. Lercher, J. Catal., 1998, 180, 56-65.
24. A. Borgna, J. Sepulveda, S. I. Magni and C. R. Apesteguia, Appl. Catal., A, 2004, 276, 207-215.
25. Hattori, Hideshi & Alabi, Wahab & Jermy, Rabindran & al-khattaf, Sulaiman. Catalysis Letters, 2013, 143. 1025-1029.
26. H. Han, M. Liu, X. W. Nie, F. S. Ding, Y. R. Wang, J. J. Li, X. W. Guo and C. S. Song, Microporous Mesoporous Mater., 2016, 234, 61-72.
27. H. Itoh, T. Hattori, K. Suzuki and Y. Murakami, J. Catal., 1983, 79, 21-33.
28. H. H. Chen, X. C. Li, G. Q. Zhao, H. B. Gu and Z. R. Zhu, Chin. J. Catal., 2015, 36, 1726-1732.
29. R. Manivannan and A. Pandurangan, Appl. Clay Sci., 2009, 44, 137-143.
30. Y. Wang, M. Y. Zhu, L. H. Kang and B. Dai, Microporous Mesoporous Mater., 2014, 196, 129-135.
31. Y. N. Sidorenko and P. N. Galich, Pet. Chem., 1991, 31, 57-69.
32. M. L. Unland, J. Phys. Chem., 1978, 82, 580-583.
33. S. T. King and J. M. Garces, J. Catal., 1987, 104, 59-70.
34. J. Garcés, G. E. Vrieland, S. Bates, F. Scheidt. 1985, Studies Surf. Sci. Cat., 20, 67
35. H. Vinek, M. Derewinski, G. Mirth, J. A. Lercher, Applied Catalysis, 1998, 68, 1, 277-284.
36. N. Giordano, L. Pino, S. Cavallaro, P. Vitarelli and B. S. Rao, Zeolites, 1987, 7, 131-134.
37. W. S. Wieland, R. J. Davis and J. M. Garces, J. Catal., 1998, 173, 490-500.
38. H. Lee, S. Lee, R. Ryoo and M. Choi, J. Catal., 2019, 373, 25-36.
39. X. S. Wang, G. Wang, D. M. Shen, C. B. Fu and M. Wei, Zeolites, 1991, 11, 254-257.
40. M. D. Sefcik, J. Am. Chem. Soc., 1979, 101, 2164-2170.
41. G. Madhavi, S. J. Kulkarni and K. V. Raghavan, J. Porous Mater., 2007, 14, 379-385.
42. N Zilkova, G. Kosova, J. Kotrla, S. Ernst and J. Cejka, in Molecular Sieves: From Basic Research to Industrial Applications, Pts A and B, ed. J. Cejka, N. Zilkova and P. Nachtigall, 2005, vol. 158, pp. 1629-1636.
43. T. Yashima, Y. Ushida, M. Ebisawa and N. Hara, J. Catal., 1975, 36, 320-326.
44. X. S. Liu, K. K. lu and J. K. Thomas, J. Phys. Chem., 1994, 98, 7877-7884.
45. J. Engelhardt, J. Szanyi and J. Valyon, J. Catal., 1987, 107, 296-306.
46. B. K. Vasanthy, M. Palanichamy and V. Krishnasamy, Appl. Catal., A, 1996, 148, 51-61.
47. D. Barthomeuf, J. Phys. Chem., 1984, 88, 42-45.
48. W. J. Mortier, J. Catal., 1978, 55, 138-145.

49. S. Hocevar and B. Drzaj, J. Catal., 1982, 73, 205-215.
50. A. K. Ghosh and G. Curthoys, J. Catal., 1984, 86, 454-456.
51. L. L. Song, Z. R. Li, R. Z. Zhang, L. F. Zhao and W. Li, Catal. Commun., 2012, 19, 90-95.
52. A. Borgna, S. Magni, J. Sepulveda, C. L. Padro and C. R. Apesteguia, Catal. Lett., 2005, 102, 15-21.
53. H. Han, M. Liu, F. S. Ding, Y. R. Wang, X. W. Guo and C. S. Song, Ind. Eng. Chem. Res., 2016, 55, 1849-1858.
54. W. O. Alabi, B. B. Tope, R. B. Jermy, A. M. Aitani, H. Hattori and S. S. Al-Khattaf, Catal. Today, 2014, 226, 117-123.
55. C. Lacroix, A. Deluzarche, A. Kiennemann and A. Boyer, Zeolites, 1984, 4, 109-111.
56. P. Kovacheva, A. Predoeva, K. Arishtirova and S. Vassilev, Appl. Catal., A, 2002, 223, 121-128.
57. T. Zhang, J. Hu and S. W. Tang, Chin. J. Chem. Eng., 2018, 26, 1513-1521.
58. M. L. Unland and G. E. Baker, U.S. Pat. No. 4,115,424, Sep. 19, 1978.
59. W. S. Wieland, R. J. Davis and J. M. Garces, Catal. Today, 1996, 28, 443-450.
60. L. L. Song, Y. Yu, Z. R. Li, S. Q. Guo, L. F. Zhao and W. Li, J. Braz. Chem. Soc., 2014, 25, 1346-1354.
61. N. K. Das and K. Pramanik, J. Indian Chem. Soc., 1997, 74, 701-704.
62. Zhang, Min & Qingyun, Yuan & Miao, & Li, Yin-Sheng & Shan, & Jia, Heming. Catalysts, 2019, 9. 829-842.
63. Z. H. Zhang, W. L. Shan, H. Li, W. C. Zhu, N. Zhang, Y. Tang, J. H. Yu, M. J. Jia, W. X. Zhang and C. L. Zhang, J. Porous Mater., 2015, 22, 1179-1186.
64. H. H. Wang, B. Wang, Y. L. Wen and W. Huang, Catal. Lett., 2017, 147, 161-166.
65. H. T. Hui, J. H. Gao, P. Liu and K. Zhang, Tianranqi Huagong, 2013, 38, 7-11.
66. F. Xu, J. F. Gu, N. J. Guan and Z. Y. Yuan, Shiyou Xuebao, 2008, 10, 346-349.
67. Q. Han, P. D. Li, Y. F. Zhang, P. Lu, L. Xu, H. C. Guo and L. Xu, ChemCatChem, 2019, 11, 1610-1614.
68. J. M. Garces, F. C. Stone, S. I. Bates, J. L. Curnutt, F. H. Scheidt and M. V. Griggs, Abstracts of Papers of the American Chemical Society, 1987, p. 194, 377-INOR.
69. N. Yamaguchi, A. Kobayashi, T. Sodesawa and F. Nozaki, React. Kinet. Catal. Lett., 1984, 25, 11-15.
70. N. Jiang, H. Jin, E. Y. Jeong and S. E. Park, J. Nanosci. Nanotechnol., 2010, 10, 227-232.
71. H. L. Chen, J. Ding and Y. M. Wang, Acta Phys.-Chim. Sin., 2013, 29, 1035-1040.
72. R. Manivannan and A. Panduranggan, Catal. Lett., 2002, 81, 119-124.
73. V. R. Vijayaraghavan and K. J. A. Raj, J. Mol. Catal. A: Chem., 2004, 207, 41-50.
74. B. Wang, W. Huang, Y. L. Wen, Z. J. Zuo, Z. H. Gao and L. H. Yin, Catal. Today, 2011, 173, 38-43.
75. B. Wang, W. Huang and Y. Wen, Energy Sources, Part A, 2011, 33, 1933-1939.
76. J. Engelhardt, J. Szanyi, J. Valyon, J. Catal., 1987, 107, 296-306.
77. Letzsch, W. & Santner, C. & Tragesser, S. Petroleum Technology Quarterly. 2008, 13. 63-67.
78. H. Hattori, A. A. Amusa, R. B. Jermy, A. M. Aitani and S. S. Al-Khattaf, J. Mol. Catal. A: Chem., 2016, 424, 98-105.

What is claimed is:

1. A method of producing styrene, comprising:
passing dimethyl-ether (DME) and toluene into a reaction chamber comprising a catalyst; wherein the catalyst comprises a zeolite comprising zeolite X or zeolite Y wherein 50-80% of the exchangeable sodium in the zeolite is replaced by Group 1 alkali metal salts of potassium, rubidium or cesium and the catalyst contains at least 0.1 wt % boron; and
reacting the DME and the toluene in the reaction chamber in the presence of the catalyst to make styrene under steady state conditions such that the catalyst has an Activity Parameter of at least 0.02 and a Selectivity Parameter of at least 0.1.

2. The method in claim 1 such that the catalyst has a Selectivity Parameter of at least 0.2.

3. The method of claim 1 wherein the reaction chamber comprises a temperature in a range 300 to 600° C.

4. The method of claim 1 wherein the step of reacting is conducted at a pressure between 1 atm and 10 atm.

5. The method of claim 1 wherein the toluene flows into the reaction chamber at a toluene WHSV between 0.1 and 10.0 $hr^{-1}$.

6. The method of claim 1 wherein the toluene is fed in a toluene feed comprising a mixture of benzene and toluene.

7. The method of claim 1 conducted at a feed DME to toluene ratio of 1.0 to 100 mol/mol.

8. The method of claim 1 wherein the toluene is fed separately in a toluene feed and the toluene feed comprises at least 90 mol % toluene.

9. The method of claim 1 where the method has a styrene selectivity of greater than 50 mol %.

10. The method of claim 1 where the method has an ethylbenzene (EB) selectivity of less than 50 mol %.

11. The method of claim 1 where the method has a toluene conversion of greater than 10%.

12. The method of claim 1 where the reaction chamber comprises a fixed-bed catalyst.

13. The method of claim 1 further comprises regenerating the catalyst in flowing air or oxygen at a temperature of at least 300° C. and a GHSV of at least 500.

14. The method of claim 1 wherein the zeolite has a Si to Al molar ratio of 1 to 10.

15. The method of claim 1 wherein the method is run continuously for a period greater than 6 hours without regenerating the catalyst.

16. The method of claim 1 wherein the catalyst contains in a range of 0.1 to 1 wt % boron.

17. The method in claim 1 such that the catalyst has an Activity Parameter in a range of 0.02 to 0.10 and a Selectivity Parameter in a range of 0.1 to 0.5.

18. The method in claim 1 such that the catalyst has an Activity Parameter of at least 0.04 and a Selectivity Parameter in a range of 0.1 to 0.4.

19. A method for making styrene comprising:
generating DME by dehydration of methanol;
providing a reaction zone containing a catalyst, wherein the catalyst comprises a zeolite comprising zeolite X or zeolite Y wherein at least 50% of the exchangeable sodium in the zeolite is replaced by Group 1 alkali metal salts of potassium, rubidium or cesium and the catalyst contains at least 0.1 wt % boron;
providing feed-streams of toluene and DME to the reaction zone;
reacting toluene and DME in the reaction zone at a temperature between 300 to 500° C. and a pressure between 1 atm and 10 atm, under steady state conditions such that the catalyst has an Activity Parameter of at least 0.02 and a Selectivity Parameter of at least 0.1, to form a first product stream comprising styrene and water;

at least partially separating the first product stream to form a styrene product stream; and removing unreacted toluene from the first product stream and recycling the unreacted toluene to the reaction zone.

20. The method of claim 19 wherein the catalyst contains at least 0.2 wt % boron.

\* \* \* \* \*